(12) United States Patent
Chow et al.

(10) Patent No.: US 10,004,796 B2
(45) Date of Patent: Jun. 26, 2018

(54) ADENOVIRAL VECTOR-BASED VACCINE AGAINST ENTEROVIRUS INFECTION

(71) Applicant: National Health Research Institutes, Zhunan Town (TW)

(72) Inventors: Yen-Hung Chow, Zhunan Town (TW); Yueh-Liang Tsou, Zhunan Town (TW); Pele Choi-Sing Chong, Zhunan Town (TW)

(73) Assignee: National Health Research Institutes, Zhunan (TW)

( * ) Notice: Subject to any disclaimer, the term of this patent is extended or adjusted under 35 U.S.C. 154(b) by 0 days. days.

(21) Appl. No.: 15/307,926

(22) PCT Filed: Mar. 26, 2015

(86) PCT No.: PCT/US2015/022738
§ 371 (c)(1),
(2) Date: Oct. 31, 2016

(87) PCT Pub. No.: WO2015/167710
PCT Pub. Date: Nov. 5, 2015

(65) Prior Publication Data
US 2017/0056491 A1    Mar. 2, 2017

Related U.S. Application Data

(60) Provisional application No. 61/985,803, filed on Apr. 29, 2014.

(51) Int. Cl.
| | |
|---|---|
| A61K 48/00 | (2006.01) |
| C12N 15/861 | (2006.01) |
| C12N 15/00 | (2006.01) |
| A61K 38/00 | (2006.01) |
| C12N 15/63 | (2006.01) |
| A61K 39/125 | (2006.01) |
| A61K 39/12 | (2006.01) |
| A61K 39/00 | (2006.01) |

(52) U.S. Cl.
CPC ............ *A61K 39/125* (2013.01); *A61K 39/12* (2013.01); *A61K 2039/5252* (2013.01); *A61K 2039/5256* (2013.01); *A61K 2039/5258* (2013.01); *A61K 2039/542* (2013.01); *A61K 2039/545* (2013.01); *A61K 2039/55566* (2013.01); *A61K 2039/57* (2013.01); *C12N 2710/10323* (2013.01); *C12N 2710/10343* (2013.01); *C12N 2770/32323* (2013.01); *C12N 2770/32334* (2013.01); *C12N 2770/32351* (2013.01); *C12N 2770/32371* (2013.01)

(58) Field of Classification Search
CPC .... A61K 2039/5252; A61K 2039/5256; A61K 2039/5258; A61K 2039/542; A61K 2039/545
See application file for complete search history.

(56) References Cited

U.S. PATENT DOCUMENTS

2003/0148511 A1* 8/2003 Ashton-Rickardt ... A61K 31/70
435/339

FOREIGN PATENT DOCUMENTS

WO    WO2013142809    *   9/2013

OTHER PUBLICATIONS

UniProt database entry A3KBJ1, A3KBJ1_9ENTO, 2007: pdf p. 1.*
UniProt number: A3KBJ1. Apr. 3, 2007.
Genbank Accession DQ060149. NCBI. Jun. 11, 2005. Wu et al.

* cited by examiner

*Primary Examiner* — Barry A Chestnut
(74) *Attorney, Agent, or Firm* — Wolf, Greenfield & Sacks, P.C.

(57) ABSTRACT

The present invention relates to a recombinant adenoviral vector for generating immunity against enterovirus infection. In one embodiment, the recombinant adenoviral vector of the invention comprises an expression cassette encoding a P1 protein and a 3 CD protease of an enterovirus. In another embodiment, the recombinant adenoviral vector of the invention comprises an expression cassette encoding a 3C protease or a 3CD protease of an enterovirus. The present invention also relates to a vaccine composition comprising the recombinant adenoviral vector as described. A method of inducing an immune response in a subject against enterovirus infection using the recombinant adenoviral vector and the vaccine composition is provided. Further provided is a method for producing virus like particles of an enterovirus by expressing the adenoviral vector as described herein in mammalian cells.

8 Claims, 22 Drawing Sheets

(A)

(B)

(C)
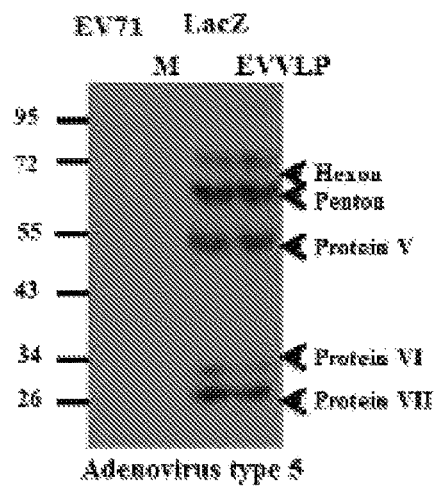
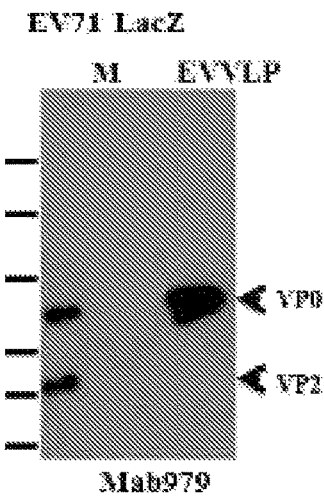
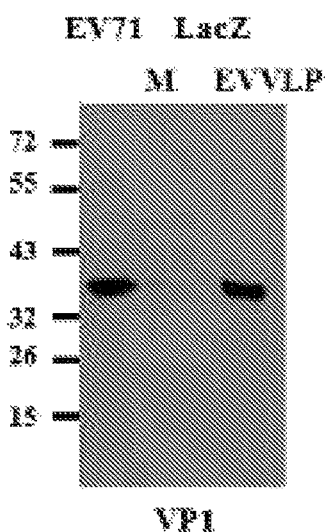
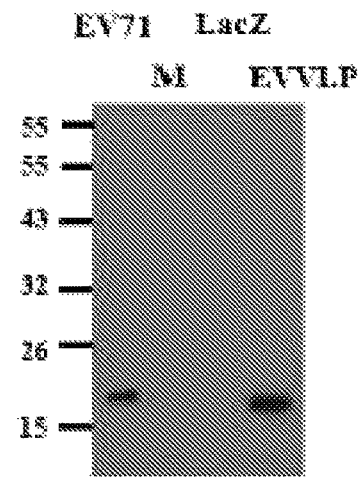
Fig. 1 (Cont')

(A)

(B)

(C)

(D)

(A)

(B)

(A)

(B)

(A)

(B)

(A)

(B)

Sequence of CMP promoter–P1 gene-IRES-3CD gene cassette

CMV promoter

TTGACGCAAATGGGCGGTAGGCGTGTACGGTGGGAGGTCTATATAAGCAGAGCTCTCTGGC

T7 promoter/priming site

TAACTAGAGAACCCACTGCTTACTGGCTTATCGAAATTAATACGACTCACTATAGGGAGACCC
AAGCTG GCTAGTTAAGCTATCAACAAGTTTGTACAAAAAAGCAGGCT

P1 gene (Strain: pinf7-54A 746..3331)

ATGGGCTCACAGGTGTCCACACAGCGCTCCGGTTCGCACGAAAACTCTAACTCAGCTACCGA
GGGTTCCACTATAAACTATACTACCATTAATTACTATAAAGATTCCTATGCCGCCACAGCAGGTA
AGCAGAGCCTTAAGCAGGACCCAGACAAGTTTGCAAATCCTGTCAAAGACATCTTCACTGAA
ATGGCAGCGCCATTAAAATCTCCATCTGCCGAGGCATGTGGTTACAGCGATCGGGTGGCACAA
TTAACTATTGGCAATTCTACCATCACTACGCAAGAAGCAGCAAACATCATAGTTGGCTATGGTG
AGTGGCCTTCCTACTGTTCGGACTCTGATGCTACTGCAGTGGACAAACCAACGCGCCCAGATG
TTTCGGTGAATAGGTTTTACACATTGGACACAAAATTGTGGGAGAAATCATCCAAGGGGTGGT
ACTGGAAATTCCCGGATGTGTTAACTGAAACCGGGGTCTTTGGTCAAAATGCACAGTTCCACT
ACCTCTATCGGTCAGGGTTCTGCATTCACGTGCAGTGCAATGCTAGTAAGTTCCACCAAGGAG
CACTCCTAGTCGCTGTCCTCCCAGAGTATGTCATTGGGACAGTGGCAGGTGGCACAGGGACG
GAGGATAGCCACCCCCCTTATAAGCAGACTCAACCCGGTGCTGATGGCTTCGAATTGCAACAC
CCGTACGTGCTTGATGCTGGCATTCCAATATCACAATTAACAGTGTGCCCACATCAGTGGATTA
ATTTGAGGACCAACAATTGTGCCACAATAATAGTGCCGTACATAAACGCACTACCCTTTGATTC
TGCCTTGAACCATTGTAACTTTGGTCTGCTGGTTGTGCCTATTAGCCCGTTAGATTATGACCAA
GGTGCGACGCCAGTGATCCCCATTACTATCACTTTGGCCCCAATGTGTTTTGAATTTGCAGGCT
TTAGACAAGCAGTTACGCAAGGGTTTCCTACTGAGTTGAAACCTGGCACAAACCAATTTTTAA
CCACTGACGATGGCGTCTCAGCACCCATTCTGCCAAACTTTCACCCCACCCCGTGTATCCATAT
ACCCGGTGAAGTTAGAAACTTGCTAGAGCTATGCCAGGTGGAGACCATTTTAGAGGTCAACA
ATGTACCTACGAATGCCACTAGCTTAATGGAGAGACTGCGCTTCCCGGTCTCAGCTCAAGCCG
GGAAAGGTGAGCTATGTGCAGTGTTCAGAGCTGACCCTGGACGAAGTGGGCCATGGCAGTC
CACCTTGTTGGGCCAGTTGTGCGGGTACTACACCCAATGGTCAGGATCACTGGAAGTCACCTT
CATGTTCACCGGGTCCTTTATGGCTACCGGCAAGATGCTCATAGCATACACACCACCAGGAGG
CCCCTTACCCAAGGACCGGGCGACCGCCATGTTGGGCACGGACGTCATCTGGGACTTTGGGC
TGCAATCGTCTGTCACTCTTGTAATACCATGGATCAGCAACACTCATTACAGAGCGCACGCTCG
AGATGGTGTGTTTGACTACTACACTACAGGTTTGGTTAGCATATGGTACCAGACGAATTATGTG
GTTCCAATTGGAGCACCCAATACAGCCTATATAATAGCATTGGCGGCAGCCCAGAAGAACTTC
ACCATGAAGTTGTGTAAGGATGCTAGTGATATCCTACAGACAGGCACTATCCAGGGAGATAGG
GTGGCAGATGTGATTGAGAGTTCTATAGGGGACAGCGTGAGCAGAGCCCTCACCCGAGCTCT
ACCGGCACCTACCGGCCAAGACACACAGGTAAGCAGCCATCGATTAGATACTGGTAAAGGTC
CAGCACTCCAAGCCGCTGAAATTGGAGCATCATCAAATGCTAGTGATGAGAGTATGATTGAGA

Fig. 14

CACGGTGTGTTCTTAATTCACATAGCACAGCTGAGACCACTCTTGATAGCTTCTTCAGCAGAG
CAGGATTAGTTGGAGAGATAGACCTCCCTCTTGAAGGCACAACCAACCCGAATGGGTACGCA
AACTGGGACATAGACATAACAGGTTACGCGCAAATGCGTAGAAAGGTGGAGCTGTTCACCTA
CATGCGTTTTAACGCAGAGATCACCTTTGTTGCATGCACCCCTACCGGGGAAGTTGTCCCGCA
ATTGCTCCAATATATGTTTGTACCACCCGGAGCCCCCAAGCCAGACTCCAGAGAATCTCTCGCA
TGGCAAACTGCCACTAATCCCTCGGTTTTTGTGAAGCTGTCAGACCCCCAGCACAGGTTTCT
GTTCCATTCATGTCACCTGCGAGCGCCTATCAATGGTTTTATGACGGGTATCCCACATTCGGTG
AACACAAACAGGAGAAAGACCTTGAATACGGGGCATGCCCAAACAACATGATGGGTACGTTC
TCAGTGCGGACTGTAGGCACCTCGAAGTCCAAGTGCCCATTGGTGATCAGGATTTACATGAG
GATGAAGCACGTCAGGGCGTGGATACCTCGCCAATGCGTAACCAGAACTATCTATTCAAAGC
CAACCCAAATTATGCTGGTAATTCTATTAAACCAACTGGTGCCAGTCGCACAGCAAT<u>GAATTC</u>
IRES
TGCATCTAGGGCGGCCAATTCCGCCCCTCTCCCTCCCCCCCCCCTAACGTTACTGGCCGAAGCC
GCTTGGAATAAGGCCGGTGTGCGTTTGTCTATATGTGATTTTCCACCATATTGCCGTCTTTTGG
CAATGTGAGGGCCCGGAAACCTGGCCCTGTCTTCTTGACGAGCATTCCTAGGGGTCTTTCCCC
TCTCGCCAAAGGAATGCAAGGTCTGTTGAATGTCGTGAAGGAAGCAGTTCCTCTGGAAGCTT
CTTGAAGACAAACAACGTCTGTAGCGACCCTTTGCAGGCAGCGGAACCCCCCACCTGGCGAC
AGGTGCCTCTGCGGCCAAAAGCCACGTGTATAAGATACACCTGCAAAGGCGGCACAACCCCA
GTGCCACGTTGTGAGTTGGATAGTTGTGGAAAGAGTCAAATGGCTCTCCTCAAGCGTATTCAA
CAAGGGGCTGAAGGATGCCCAGAAGGTACCCCATTGTATGGGATCTGATCTGGGGCCTCGGT
GCACATGCTTTACATGTGTTTAGTCGAGGTTAAAAAAACGTCTAGGCCCCCCGAACCACGGG
GACGTGGTTTTCCTTTGAAAAACACGATGATAAGCTTGCCA<u>GCGGCCGC</u>
3CD gene (Strain: pinf7-S4A 5390..7324)
GGGCCGAGCTTGGACTTCGCCCTATCTCTACTTAGGAGGAACATTAGGCAGGTCCAAACCGA
CCAGGGCCACTTTACAATGTTAGGAGTGCGAGACCGCTTGGCTGTGCTCCCCAGACACTCCC
AACCAGGAAAGACCATCTGGGTTGAACACAAATTAGTGAAGATCGTAGATGCTGTGGAGTTA
GTAGACGAACAAGGGGTTAACTTAGAGCTCACACTGGTAACGCTTGATAC

```
TTTTGGATCCAACAACTCGCGATGTCAGCAAGATGAAATTCTACATGGACAAGTATGGGTTGG
ATCTACCGTACTCTACTTATGTTAAAGATGAACTTAGGGCCATCGACAAGATCAAGAAAGGGA
AGTCTCGTCTCATAGAAGCGAGCAGTCTAAATGACTCAGTGTACTTGAGAATGACATTTGGGC
ACCTTTATGAAGCTTTCCACGCCAATCCAGGTACAATCACTGGTTCAGCTGTTGGGTGCAACC
CAGATGTGTTCTGGAGCAAGTTACCAATTCTACTTTCAGGATCGCTTTTCGCGTTTGACTACTC
GGGGTATGACGCTAGTCTCAGCCCAGTGTGGTTCAGGGCGCTGGAGATAGTCCTGCGGGAAA
TTGGATACTCCGAAGACGCAGTGTCTCTCATAGAAGGGATCAATCACACCCATCATGTGTACCG
CAATAAAACTTATTGTGTTCTTGGGGGAATGCCCTCAGGTTGCTCAGGCACCTCCATTTTCAAC
TCGATGATCAACAATATCATTATTAGAACACTCCTGATTAAAACATTCAAAGGGATAGATCTAAA
TGAACTGAACATGGTGGCCTACGGGGATGATGTGTTGGCTAGTTACCCCTTCCCAATTGACTG
TCTGGAGTTGGCAAGAACAGGCAAGGAGTATGGTCTAACTATGACCCCTGCCGACAAGTCAC
CCTGCTTTAATGAGGTTACGTGGGAGAATGCCACTTTCTTGAAGAGAGGATTCTTGCCTGATT
ATCAATTCCCGTTTCTCATCCACCCTACGATGCCAATGAGGGAGATTCACGAATCCATTCGTTG
GACCAAAGATGCACGAAGTACTCAAGATCACGTGCGCTCCCTCTGCTTATTAGCATGGCTCAA
CGGGAAGAGGAGTATGAAAAATTTGTGAGTGCAATCAGATCAGTTCCAATTGGAAAAGCAT
TGGCTA TACCAAATTATGAGAATCTGAGGAGAAATTGGCTCGAATTGTTTT
```

Fig. 14 (cont')

Sequence of CMP promoter—P1 gene-EF-1α promoter-3CD gene cassette

CMV promoter

<u>TTGACGCAAATGGGCGGTAGGCGTGTACGGTGGGAGGTCTATATAAGCAGAGCTCTCTGGC</u>

T7 promoter/priming site

TAACTAGAGAACCCACTGCTTACTGGCTTATCGAAAT<u>TAATACGACTCACTATAGGG</u>AGACCC
AAGCTG GCTAGTTAAGCTATCAACAAGTTTGTACAAAAAAGCAGGCT

P1 gene (Strain: pInf7-S4A 746..3331)

ATGGGCTCACAGGTGTCCACACAGCGCTCCGGTTCGCACGAAAACTCTAACTCAGCTACCGA
GGGTTCCACTATAAACTATACTACCATTAATTACTATAAAGATTCCTATGCCGCCACAGCAGGTA
AGCAGAGCCTTAAGCAGGACCCAGACAAGTTTGCAAATCCTGTCAAAGACATCTTCACTGAA
ATGGCAGCGCCATTAAAATCTCCATCTGCCGAGGCATGTGGTTACAGCGATCGGGTGGCACAA
TTAACTATTGGCAATTCTACCATCACTACGCAAGAAGCAGCAAACATCATAGTTGGCTATGGTG
AGTGGCCTTCCTACTGTTCGGACTCTGATGCTACTGCAGTGGACAAACCAACGCGCCCAGATG
TTTCGGTGAATAGGTTTTACACATTGGACACAAAATTGTGGGAGAAATCATCCAAGGGGTGGT
ACTGGAAATTCCCGGATGTGTTAACTGAAACCGGGGTCTTTGGTCAAAATGCACAGTTCCACT
ACCTCTATCGGTCAGGGTTCTGCATTCACGTGCAGTGCAATGCTAGTAAGTTCCACCAAGGAG
CACTCCTAGTCGCTGTCCTCCCAGAGTATGTCATTGGGACAGTGGCAGGTGGCACAGGGACG
GAGGATAGCCACCCCCCTTATAAGCAGACTCAACCCGGTGCTGATGGCTTCGAATTGCAACAC
CCGTACGTGCTTGATCTGGCATTCCAATATCACAATTAACAGTGTGCCCACATCAGTGGATTA
ATTTGAGGACCAACAATTGTGCCACAATAATAGTGCCGTACATAAACGCACTACCCTTTGATTC
TGCCTTGAACCATTGTAACTTTGGTCTGCTGGTTGTGCCTATTAGCCCGTTAGATTATGACCAA
GGTGCGACGCCAGTGATCCCCATTACTATCACTTTGGCCCCAATGTGTTTTGAATTTGCAGGCT
TTAGACAAGCAGTTACGCAAGGGTTTCCTACTGAGTTGAAACCTGGCACAAACCAATTTTTAA
CCACTGACGATGGCGTCTCAGCACCCATTCTGCCAAACTTTCACCCCACCCCGTGTATCCATAT
ACCCGGTGAAGTTAGAAACTTGCTAGAGCTATGCCAGGTGGAGACCATTTTAGAGGTCAACA
ATGTACCTACGAATGCCACTAGCTTAATGGAGAGACTGCGCTTCCCGGTCTCAGCTCAAGCCG
GGAAAGGTGAGCTATGTGCAGTGTTCAGAGCTGACCCTGGACGAAGTGGGCCATGGCAGTC
CACCTTGTTGGGCCAGTTGTGCGGGTACTACACCCAATGGTCAGGATCACTGGAAGTCACCTT
CATGTTCACCGGGTCCTTTATGGCTACCGGCAAGATGCTCATAGCATACACACCACCAGGAGG
CCCCTTACCCAAGGACCGGGCGACCGCCATGTTGGGCACGGACGTCATCTGGGACTTTGGGC
TGCAATCGTCTGTCACTCTTGTAATACCATGGATCAGCAACACTCATTACAGAGCGCACGCTCG
AGATGGTGTGTTTGACTACTACACTACAGGTTTGGTTAGCATATGGTACCAGACGAATTATGTG
GTTCCAATTGGAGCACCCAATACAGCCTATATAATAGCATTGGCGGCAGCCCAGAAGAACTTC
ACCATGAAGTTGTGTAAGGATGCTAGTGATATCCTACAGACAGGCACTATCCAGGGAGATAGG
GTGGCAGATGTGATTGAGAGTTCTATAGGGGACAGCGTGAGCAGAGCCCTCACCCGAGCTCT
ACCGGCACCTACCGGCCAAGACACACAGGTAAGCAGCCATCGATTAGATACTGGTAAAGGTC

Fig. 15

CAGCACTCCAAGCCGCTGAAATTGGAGCATCATCAAATGCTAGTGATGAGAGTATGATTGAGA
CACGGTGTGTTCTTAATTCACATAGCACAGCTGAGACCACTCTTGATAGCTTCTTCAGCAGAG
CAGGATTAGTTGGAGAGATAGACCTCCCTCTTGAAGGCACAACCAACCCGAATGGGTACGCA
AACTGGGACATAGACATAACAGGTTACGCGCAAATGCGTAGAAAGGTGGAGCTGTTCACCTA
CATGCGTTTTAACGCAGAGATCACCTTTGTTGCATGCACCCCTACCGGGGAAGTTGTCCCGCA
ATTGCTCCAATATATGTTTGTACCACCCGGAGCCCCCAAGCCAGACTCCAGAGAATCTCTCGCA
TGGCAAACTGCCACTAATCCCTCGGTTTTTGTGAAGCTGTCAGACCCCCCAGCACAGGTTTCT
GTTCCATTCATGTCACCTGCGAGCGCCTATCAATGGTTTTATGACGGGTATCCCACATTCGGTG
AACACAAACAGGAGAAAGACCTTGAATACGGGGCATGCCCAAACAACATGATGGGTACGTTC
TCAGTGCGGACTGTAGGCACCTCGAAGTCCAAGTGCCCATTGGTGATCAGGATTTACATGAG
GATGAAGCACGTCAGGGCGTGGATACCTCGCCCAATGCGTAACCAGAACTATCTATTCAAAGC
CAACCCAAATTATGCTGGTAATTCTATTAAACCAACTGGTGCCAGTCGCACAGCAAT<u>GAATTC</u>

EF-1α promoter

GTGAGGCTCCGGTGCCCGTCAGTGGGCAGAGCGCACATCGCCCACAGTCCCCGAGAAGTTG
GGGGGAGGGGTCGGCAATTGAACCGGTGCCTAGAGAAGGTGGCGCGGGGTAAACTGGGA
AAGTGATGTCGTGTACTGGCTCCGCCTTTTTCCCGAGGGTGGGGGAGAACCGTATATAAGTGC
AGTAGTCGCCGTGAACGTTCTTTTTCGCAACGGGTTTGCCGCCAGAACACAGGTAAGTGCCG
TGTGTGGTTCCCGCGGGCCTGGCCTCTTTACGGGTTATGGCCCTTGCGTGCCTTGAATTACTTC
CACCTGGCTGCAGTACGTGATTCTTGATCCCGAGCTTCGGGTTGGAAGTGGGTGGGAGAGTT
CGAGGCCTTGCGCTTAAGGAGCCCCTTCGCCTCGTGCTTGAGTTGAGGCCTGGCCTGGGCGC
TGGGGCCGCCGCGTGCGAATCTGGTGGCACCTTCGCGCCTGTCTCGCTGCTTTCGATAAGTCT
CTAGCCATTTAAAATTTTTGATGACCTGCTGCGACGCTTTTTTTCTGGCAAGATAGTCTTGTAA
ATGCGGGCCAAGATCTGCACACTGGTATTTCGGTTTTTGGGGTCGCGGGCGGCGACGGGGC
CCGTGCGTCCCAGCGCACATGTTCGGCGAGGCGGGGCCTGCGAGCGCGGCCACCGAGAATC
GGACGGGGGTAGTCTCAAGCTGGCCGGCCTGCTCTGGTGCCTGGCCTCGCGCCGCCGTGTAT
CGCCCCGCCCTGGGCGGCAAGGCTGGCCCGGTCGGCACCAGTTGCGTGAGCGGAAAGATG
GCCGCTTCCCGGCCCTGCTGCAGGGAGCTCAAAATGGAGGACGCGGCGCTCGGGAGAGCG
GGCGGGTGAGTCACCCACACAAAGGAAAAGGGCCTTTCCGTCCTCAGCCGTCGCTTCATGTG
ACTCCACGGAGTACCGGGCGCCGTCCAGGCACCTCGATTAGTTCTCGAGCTTTTGGAGTACG
TCGTCTTTAGGTTGGGGGGAGGGGTTTTATGCGATGGAGTTTCCCCACACTGAGTGGGTGGA
GACTGAAGTTAGGCCAGCTTGGCACTTGATGTAATTCTCCTTGGAATTTGCCCTTTTTGAGTTT
GGATCTTGGTTCATTCTCAAGCCTCAGACAGTGGTTCAAAGTTTTTTTCTTCCATTTCAGGTGT
CGTGAAAA <u>GCGGCCGC</u>

3CD gene (Strain: pinf7-S4A 5390..7324)

GGGCCGAGCTTGGACTTCGCCCTATCTCTACTTA

AGAGACATCACAAGATTCATACCAGAAACAATTAGTCCTGCTAGTGATGCCACTTTAGTTATAA
ATACTGAACATATGCCCAGTATGTTTGTGCCAGTTGGAGATGTGGTCCAGTATGGGTTTTTGAA
CCTTAGTGGTAAGCCCACTCACAGGACTATGATGTACAATTTCCCAACAAAAGCAGGACAGTG
TGGTGGTGTTGTGACTGCCGTGGGTAAAGTGATTGGGATCCACATTGGTGGCAACGGTAGAC
AAGGTTTCTGCGCTGCCCTGAAGAGGGGATACTTTTGCAGTGAACAAGGTGAGATCCAATGG
ATGAAGCCCAACAAAGAAACTGGCAGGTTGAACATCAACGGACCTACTCGCACTAAGCTTGA
ACCAAGTGTCTTTCACGATGTGTTCGAAGGCACTAAAGAGCCAGCAGTGCTGACTAGTAAAG
ACCCAAGGCTGGAAGTTGACTTTGAACAGGCTCTTTTTTCAAAATACGTGGGGAACACGCTT
CATGAACCCGACGAGTTTGTCAAGGAGGCGGCCCTACATTATGCCAACCAACTCAAGCAGTT
AGATATCAAGACCACCAAGATGAGCATGGAGGATGCATGTTACGGCACAGAGAACCTGGAAG
CTATAGATCTTCACACAAGTGCAGGATATCCATACAGTGCACTAGGCATCAAGAAAAAGGACA
TTTTGGATCCAACAACTCGCGATGTCAGCAAGATGAAATTCTACATGGACAAGTATGGGTTGG
ATCTACCGTACTCTACTTATGTTAAAGATGAACTTAGGGCCATCGACAAGATCAAGAAAGGGA
AGTCTCGTCTCATAGAAGCGAGCAGTCTAAATGACTCAGTGTACTTGAGAATGACATTTGGGC
ACCTTTATGAAGCTTTCCACGCCAATCCAGGTACAATCACTGGTTCAGCTGTTGGGTGCAACC
CAGATGTGTTCTGGAGCAAGTTACCAATTCTACTTTCAGGATCGCTTTTCGCGTTTGACTACTC
GGGGTATGACGCTAGTCTCAGCCCAGTGTGGTTCAGGGCGCTGGAGATAGTCCTGCGGGAAA
TTGGATACTCCGAAGACGCAGTGTCTCTCATAGAAGGGATCAATCACACCCATCATGTGTACCG
CAATAAAACTTATTGTGTTCTTGGGGAATGCCCTCAGGTTGCTCAGGCACCTCCATTTTCAAC
TCGATGATCAACAATATCATTATTAGAACACTCCTGATTAAAACATTCAAAGGGATAGATCTAAA
TGAACTGAACATGGTGGCCTACGGGATGATGTGTTGGCTAGTTACCCCTTCCCAATTGACTG
TCTGGAGTTGGCAAGAACAGGCAAGGAGTATGGTCTAACTATGACCCCTGCCGACAAGTCAC
CCTGCTTTAATGAGGTTACGTGGGAGAATGCCACTTTCTTGAAGAGGATTCTTGCCTGATT
ATCAATTCCCGTTTCTCATCCACCCTACGATGCCAATGAGGGAGATTCACGAATCCATTCGTTG
GACCAAAGATGCACGAAGTACTCAAGATCACGTGCGCTCCCTCTGCTTATTAGCATGGCTCAA
CGGGAAGAGGAGTATGAAAAATTTGTGAGTGCAATCAGATCAGTTCCAATTGGAAAAGCAT
TGGCTA TACCAAATTATGAGAATCTGAGGAGAAATTGGCTCGAATTGTTTT

Fig. 15 (cont')

- 3C amino acid sequence (183 A.A)

GPSLDFALSLLRRNIRQVQTDQGHFTMLGVRDRLAVLPRHSQPGKTIWVEHKL
VKIVDAVELVDEQGVNLELTLVTLDTNEKFRDITRFIPETISPASDATLVINT
EHMPSMFVPVGDVVQYGFLNLSGKPTHRTMMYNFPTKAGQCGGVVTAVGKVIG
IHIGGNGRQGFCAALKRGYFCSEQ

- 3D amino acid sequence (462 A.A)

GEIQWMKPNKETGRLNINGPTRTKLEPSVFHDVFEGTKEPAVLTSKDPRLEVD
FEQALFSKYVGNTLHEPDEFVKEAALHYANQLKQLDIKTTKMSMEDACYGTEN
LEAIDLHTSAGYPYSALGIKKKDILDPTTRDVSKMKFYMDKYGLDLPYSTYVK
DELRAIDKIKKGKSRLIEASSLNDSVYLRMTFGHLYEAFHANPGTITGSAVGC
NPDVFWSKLPILLSGSLFAFDYSGYDASLSPVWFRALEIVLREIGYSEDAVSL
IEGINHTHHVYRNKTYCVLGGMPSGCSGTSIFNSMINNIIIRTLLIKTFKGID
LNELNMVAYGDDVLASYPFPIDCLELARTGKEYGLTMTPADKSPCFNEVTW
ENATFLKRGFLPDYQFPFLIHPTMPMREIHESIRWTKDARSTQDHVRSLCLLA
WLNGKEE YEKFVSAIRSVPIGKALAIPNYENLRRNWLELF

- 3CD amino acid sequence (645 A.A)

GPSLDFALSLLRRNIRQVQTDQGHFTMLGVRDHLAVLPRHSQPG
KTIWVEHKLVKIVDAVELVDEQGVNLELTLITLDTNEKFRDITRFIPETINPASDATL
VINTEHMPSMFVPVGDVVQYGFLNLSGKPTHRTMMYNFPTKAGQCGGVVTAVGKVIGI
HIGGNGRQGFCAALKRGYFCSEQGEIQWMKSNKETGRLNINGPTRTKLEPSVFHDVFE
GTKEPAVLTSKDPRLEVDFEQALFSKYVGNTLHEPDEFVKEAALHYANQLKQLDIKTT
KMSMEDACYGTENLEAIDLHTSAGYPYSALGIKKKDILDPTTRDVSRMKFYMDKYGLD
LPYSTYVKDELRAIDKIKKGKSRLIEASSLNDSVYLRMTFGHLYEAFHANPGTVTGSA
VGCNPDVFWSKLPILLPGSLFAFDYSGYDASLSPVWFRALEIVLREIGYSEDAVSLIE
GINHTHHVYRNKTYCVLGGMPSGCSGTSIFNSMINNIIIRTLLIKTFKGIDLDELNMV
AYGDDVLASYPFPIDCLELARTGKEYGLTMTPADKSPCFNEVTWENATFLKRGFLPDH
QFPFLIHPTMPMREIHESIRWTKDARNTQDHVRSLCLLAWHNGKEEYEKFVSTIRSVP
IGKALAIPNFENLRRNWLELF

MGSQVSTQRSGSHENSNSATEGSTINYTTINYYKDSYAATAGKQSLKQDPDKFANPVKDI
FTEMAAPLKSPSAEACGYSDRVAQLTIGNSTITTQEAANIIVGYGEWPSYCSDSDATAVD
KPTRPDVSVNRFYTLDTKLWEKSSKGWYWKFPDVLTETGVFGQNAQFHYLYRSGFCIHVQ
CNASKFHQGALLVAVLPEYVIGTVAGGTGTEDSHPPYKQTQPGADGFELQHPYVLDAGIP
ISQLTVCPHQWINLRTNNCATIIVPYINALPFDSALNHCNFGLLVVPISPLDYDQGATPV
IPITITLAPMCFEFAGFRQAVTQGFPTELKPGTNQFLTTDDGVSAPILPNFHPTPCIHIP
GEVRNLLELCQVETILEVNNVPTNATSLMERLRFPVSAQAGKGELCAVFRADPGRSGPWQ
STLLGQLCGYYTQWSGSLEVTFMFTGSFMATGKMLIAYTPPGGPLPKDRATAMLGTDVIW
DFGLQSSVTLVIPWISNTHYRAHARDGVFDYYTTGLVSIWYQTNYVVPIGAPNTAYIIAL
AAAQKNFTMKLCKDASDILQTGTIQGDRVADVIESSIGDSVSRALTRALPAPTGQDTQVS
SHRLDTGKGPALQAAEIGASSNASDESMIETRCVLNSHSTAETTLDSFFSRAGLVGEIDL
PLEGTTNPNGYANWDIDITGYAQMRRKVELFTYMRFNAEITFVACTPTGEVVPQLLQYMF
VPPGAPKPDSRESLAWQTATNPSVFVKLSDPPAQVSVPFMSPASAYQWFYDGYPTFGEHK
QEKDLEYGACPNNMMGTFSVRTVGTSKSKCPLVIRIYMRMKHVRAWIPRPMRNQNYLFKA
NPNYAGNSIKPTGASRTAITTL

Fig. 17

SEQUENCE LISTING

<160> NUMBER OF SEQ ID NOS: 16

<210> SEQ ID NO 1
<211> LENGTH: 862
<212> TYPE: PRT
<213> ORGANISM: Enterovirus 71

<400> SEQUENCE: 1

```
Met Gly Ser Gln Val Ser Thr Gln Arg Ser Gly Ser His Glu Asn Ser
1               5                   10                  15

Asn Ser Ala Thr Glu Gly Ser Thr Ile Asn Tyr Thr Thr Ile Asn Tyr
            20                  25                  30

Tyr Lys Asp Ser Tyr Ala Ala Thr Ala Gly Lys Gln Ser Leu Lys Gln
        35                  40                  45

Asp Pro Asp Lys Phe Ala Asn Pro Val Lys Asp Ile Phe Thr Glu Met
    50                  55                  60

Ala Ala Pro Leu Lys Ser Pro Ser Ala Glu Ala Cys Gly Tyr Ser Asp
65                  70                  75                  80

Arg Val Ala Gln Leu Thr Ile Gly Asn Ser Thr Ile Thr Thr Gln Glu
                85                  90                  95

Ala Ala Asn Ile Ile Val Gly Tyr Gly Glu Trp Pro Ser Tyr Cys Ser
            100                 105                 110

Asp Ser Asp Ala Thr Ala Val Asp Lys Pro Thr Arg Pro Asp Val Ser
        115                 120                 125

Val Asn Arg Phe Tyr Thr Leu Asp Thr Lys Leu Trp Glu Lys Ser Ser
    130                 135                 140

Lys Gly Trp Tyr Trp Lys Phe Pro Asp Val Leu Thr Glu Thr Gly Val
145                 150                 155                 160

Phe Gly Gln Asn Ala Gln Phe His Tyr Leu Tyr Arg Ser Gly Phe Cys
                165                 170                 175

Ile His Val Gln Cys Asn Ala Ser Lys Phe His Gln Gly Ala Leu Leu
            180                 185                 190

Val Ala Val Leu Pro Glu Tyr Val Ile Gly Thr Val Ala Gly Gly Thr
        195                 200                 205

Gly Thr Glu Asp Ser His Pro Pro Tyr Lys Gln Thr Gln Pro Gly Ala
    210                 215                 220

Asp Gly Phe Glu Leu Gln His Pro Tyr Val Leu Asp Ala Gly Ile Pro
225                 230                 235                 240

Ile Ser Gln Leu Thr Val Cys Pro His Gln Trp Ile Asn Leu Arg Thr
                245                 250                 255

Asn Asn Cys Ala Thr Ile Ile Val Pro Tyr Ile Asn Ala Leu Pro Phe
            260                 265                 270

Asp Ser Ala Leu Asn His Cys Asn Phe Gly Leu Leu Val Val Pro Ile
        275                 280                 285

Ser Pro Leu Asp Tyr Asp Gln Gly Ala Thr Pro Val Ile Pro Ile Thr
    290                 295                 300

Ile Thr Leu Ala Pro Met Cys Phe Glu Phe Ala Gly Phe Arg Gln Ala
305                 310                 315                 320

Val Thr Gln Gly Phe Pro Thr Glu Leu Lys Pro Gly Thr Asn Gln Phe
                325                 330                 335

Leu Thr Thr Asp Asp Gly Val Ser Ala Pro Ile Leu Pro Asn Phe His
            340                 345                 350

Pro Thr Pro Cys Ile His Ile Pro Gly Glu Val Arg Asn Leu Leu Glu
        355                 360                 365

Leu Cys Gln Val Glu Thr Ile Leu Glu Val Asn Asn Val Pro Thr Asn
    370                 375                 380

Ala Thr Ser Leu Met Glu Arg Leu Arg Phe Pro Val Ser Ala Gln Ala
385                 390                 395                 400

Gly Lys Gly Glu Leu Cys Ala Val Phe Arg Ala Asp Pro Gly Arg Ser
                405                 410                 415
```

-continued

Gly Pro Trp Gln Ser Thr Leu Leu Gly Gln Leu Cys Gly Tyr Tyr Thr
            420                 425                 430

Gln Trp Ser Gly Ser Leu Glu Val Thr Phe Met Phe Thr Gly Ser Phe
        435                 440                 445

Met Ala Thr Gly Lys Met Leu Ile Ala Tyr Thr Pro Pro Gly Gly Pro
    450                 455                 460

Leu Pro Lys Asp Arg Ala Thr Ala Met Leu Gly Thr Asp Val Ile Trp
465                 470                 475                 480

Asp Phe Gly Leu Gln Ser Ser Val Thr Leu Val Ile Pro Trp Ile Ser
                485                 490                 495

Asn Thr His Tyr Arg Ala His Ala Arg Asp Gly Val Phe Asp Tyr Tyr
            500                 505                 510

Thr Thr Gly Leu Val Ser Ile Trp Tyr Gln Thr Asn Tyr Val Val Pro
        515                 520                 525

Ile Gly Ala Pro Asn Thr Ala Tyr Ile Ile Ala Leu Ala Ala Ala Gln
    530                 535                 540

Lys Asn Phe Thr Met Lys Leu Cys Lys Asp Ala Ser Asp Ile Leu Gln
545                 550                 555                 560

Thr Gly Thr Ile Gln Gly Asp Arg Val Ala Asp Val Ile Glu Ser Ser
                565                 570                 575

Ile Gly Asp Ser Val Ser Arg Ala Leu Thr Arg Ala Leu Pro Ala Pro
            580                 585                 590

Thr Gly Gln Asp Thr Gln Val Ser Ser His Arg Leu Asp Thr Gly Lys
        595                 600                 605

Gly Pro Ala Leu Gln Ala Ala Glu Ile Gly Ala Ser Ser Asn Ala Ser
    610                 615                 620

Asp Glu Ser Met Ile Glu Thr Arg Cys Val Leu Asn Ser His Ser Thr
625                 630                 635                 640

Ala Glu Thr Thr Leu Asp Ser Phe Phe Ser Arg Ala Gly Leu Val Gly
                645                 650                 655

Glu Ile Asp Leu Pro Leu Glu Gly Thr Thr Asn Pro Asn Gly Tyr Ala
            660                 665                 670

Asn Trp Asp Ile Asp Ile Thr Gly Tyr Ala Gln Met Arg Arg Lys Val
        675                 680                 685

Glu Leu Phe Thr Tyr Met Arg Phe Asn Ala Glu Ile Thr Phe Val Ala
    690                 695                 700

Cys Thr Pro Thr Gly Glu Val Val Pro Gln Leu Leu Gln Tyr Met Phe
705                 710                 715                 720

Val Pro Pro Gly Ala Pro Lys Pro Asp Ser Arg Glu Ser Leu Ala Trp
                725                 730                 735

Gln Thr Ala Thr Asn Pro Ser Val Phe Val Lys Leu Ser Asp Pro Pro
            740                 745                 750

Ala Gln Val Ser Val Pro Phe Met Ser Pro Ala Ser Ala Tyr Gln Trp
        755                 760                 765

Phe Tyr Asp Gly Tyr Pro Thr Phe Gly Glu His Lys Gln Glu Lys Asp
    770                 775                 780

Leu Glu Tyr Gly Ala Cys Pro Asn Asn Met Met Gly Thr Phe Ser Val
785                 790                 795                 800

Arg Thr Val Gly Thr Ser Lys Ser Lys Cys Pro Leu Val Ile Arg Ile
                805                 810                 815

Tyr Met Arg Met Lys His Val Arg Ala Trp Ile Pro Arg Pro Met Arg
            820                 825                 830

```
Asn Gln Asn Tyr Leu Phe Lys Ala Asn Pro Asn Tyr Ala Gly Asn Ser
            835                 840                 845

Ile Lys Pro Thr Gly Ala Ser Arg Thr Ala Ile Thr Thr Leu
    850                 855                 860

<210> SEQ ID NO 2
<211> LENGTH: 645
<212> TYPE: PRT
<213> ORGANISM: Enterovirus 71

<400> SEQUENCE: 2

Gly Pro Ser Leu Asp Phe Ala Leu Ser Leu Leu Arg Arg Asn Ile Arg
1               5                   10                  15

Gln Val Gln Thr Asp Gln Gly His Phe Thr Met Leu Gly Val Arg Asp
            20                  25                  30

His Leu Ala Val Leu Pro Arg His Ser Gln Pro Gly Lys Thr Ile Trp
        35                  40                  45

Val Glu His Lys Leu Val Lys Ile Val Asp Ala Val Glu Leu Val Asp
    50                  55                  60

Glu Gln Gly Val Asn Leu Glu Leu Thr Leu Ile Thr Leu Asp Thr Asn
65                  70                  75                  80

Glu Lys Phe Arg Asp Ile Thr Arg Phe Ile Pro Glu Thr Ile Asn Pro
                85                  90                  95

Ala Ser Asp Ala Thr Leu Val Ile Asn Thr Glu His Met Pro Ser Met
            100                 105                 110

Phe Val Pro Val Gly Asp Val Val Gln Tyr Gly Phe Leu Asn Leu Ser
        115                 120                 125

Gly Lys Pro Thr His Arg Thr Met Met Tyr Asn Phe Pro Thr Lys Ala
    130                 135                 140

Gly Gln Cys Gly Gly Val Val Thr Ala Val Gly Lys Val Ile Gly Ile
145                 150                 155                 160

His Ile Gly Gly Asn Gly Arg Gln Gly Phe Cys Ala Ala Leu Lys Arg
                165                 170                 175

Gly Tyr Phe Cys Ser Glu Gln Gly Glu Ile Gln Trp Met Lys Ser Asn
            180                 185                 190

Lys Glu Thr Gly Arg Leu Asn Ile Asn Gly Pro Thr Arg Thr Lys Leu
        195                 200                 205

Glu Pro Ser Val Phe His Asp Val Phe Glu Gly Thr Lys Glu Pro Ala
    210                 215                 220

Val Leu Thr Ser Lys Asp Pro Arg Leu Glu Val Asp Phe Glu Gln Ala
225                 230                 235                 240

Leu Phe Ser Lys Tyr Val Gly Asn Thr Leu His Glu Pro Asp Glu Phe
                245                 250                 255

Val Lys Glu Ala Ala Leu His Tyr Ala Asn Gln Leu Lys Gln Leu Asp
            260                 265                 270

Ile Lys Thr Thr Lys Met Ser Met Glu Asp Ala Cys Tyr Gly Thr Glu
        275                 280                 285

Asn Leu Glu Ala Ile Asp Leu His Thr Ser Ala Gly Tyr Pro Tyr Ser
    290                 295                 300

Ala Leu Gly Ile Lys Lys Lys Asp Ile Leu Asp Pro Thr Thr Arg Asp
305                 310                 315                 320

Val Ser Arg Met Lys Phe Tyr Met Asp Lys Tyr Gly Leu Asp Leu Pro
                325                 330                 335

Tyr Ser Thr Tyr Val Lys Asp Glu Leu Arg Ala Ile Asp Lys Ile Lys
            340                 345                 350
```

Lys Gly Lys Ser Arg Leu Ile Glu Ala Ser Ser Leu Asn Asp Ser Val
355                 360                 365

Tyr Leu Arg Met Thr Phe Gly His Leu Tyr Glu Ala Phe His Ala Asn
370                 375                 380

Pro Gly Thr Val Thr Gly Ser Ala Val Gly Cys Asn Pro Asp Val Phe
385                 390                 395                 400

Trp Ser Lys Leu Pro Ile Leu Leu Pro Gly Ser Leu Phe Ala Phe Asp
                405                 410                 415

Tyr Ser Gly Tyr Asp Ala Ser Leu Ser Pro Val Trp Phe Arg Ala Leu
                420                 425                 430

Glu Ile Val Leu Arg Glu Ile Gly Tyr Ser Glu Asp Ala Val Ser Leu
                435                 440                 445

Ile Glu Gly Ile Asn His Thr His His Val Tyr Arg Asn Lys Thr Tyr
450                 455                 460

Cys Val Leu Gly Gly Met Pro Ser Gly Cys Ser Gly Thr Ser Ile Phe
465                 470                 475                 480

Asn Ser Met Ile Asn Asn Ile Ile Ile Arg Thr Leu Leu Ile Lys Thr
                485                 490                 495

Phe Lys Gly Ile Asp Leu Asp Glu Leu Asn Met Val Ala Tyr Gly Asp
                500                 505                 510

Asp Val Leu Ala Ser Tyr Pro Phe Pro Ile Asp Cys Leu Glu Leu Ala
                515                 520                 525

Arg Thr Gly Lys Glu Tyr Gly Leu Thr Met Thr Pro Ala Asp Lys Ser
                530                 535                 540

Pro Cys Phe Asn Glu Val Thr Trp Glu Asn Ala Thr Phe Leu Lys Arg
545                 550                 555                 560

Gly Phe Leu Pro Asp His Gln Phe Pro Phe Leu Ile His Pro Thr Met
                565                 570                 575

Pro Met Arg Glu Ile His Glu Ser Ile Arg Trp Thr Lys Asp Ala Arg
                580                 585                 590

Asn Thr Gln Asp His Val Arg Ser Leu Cys Leu Leu Ala Trp His Asn
                595                 600                 605

Gly Lys Glu Glu Tyr Glu Lys Phe Val Ser Thr Ile Arg Ser Val Pro
610                 615                 620

Ile Gly Lys Ala Leu Ala Ile Pro Asn Phe Glu Asn Leu Arg Arg Asn
625                 630                 635                 640

Trp Leu Glu Leu Phe
                645

<210> SEQ ID NO 3
<211> LENGTH: 5302
<212> TYPE: DNA
<213> ORGANISM: Artificial Sequence
<220> FEATURE:
<223> OTHER INFORMATION: expression cassette

<400> SEQUENCE: 3
ttgacgcaaa tgggcggtag gcgtgtacgg tgggaggtct atataagcag agctctctgg      60
ctaactagag aacccactgc ttactggctt atcgaaatta atacgactca ctataggag     120 acccaagctg gctagttaag ctatcaacaa gtttgtacaa aaaagcaggc tatgggctca     180
caggtgtcca cacagcgctc cggttcgcac gaaaactcta actcagctac cgagggttcc     240
actataaact atactaccat taattactat aaagattcct atgccgccac agcaggtaag     300
cagagcctta agcaggaccc agacaagttt gcaaatcctg tcaaagacat cttcactgaa     360

-continued

```
atggcagcgc cattaaaatc tccatctgcc gaggcatgtg gttacagcga tcgggtggca    420
caattaacta ttggcaattc taccatcact acgcaagaag cagcaaacat catagttggc    480
tatggtgagt ggccttccta ctgttcggac tctgatgcta ctgcagtgga caaaccaacg    540
cgcccagatg tttcggtgaa taggttttac acattggaca caaaattgtg ggagaaatca    600 tccaagggt ggtactggaa attcccggat gtgttaactg aaaccggggt ctttggtcaa     660
aatgcacagt tccactacct ctatcggtca gggttctgca ttcacgtgca gtgcaatgct    720
agtaagttcc accaaggagc actcctagtc gctgtcctcc cagagtatgt cattgggaca    780
gtggcaggtg gcacagggac ggaggatagc cacccccctt ataagcagac tcaacccggt    840
gctgatggct tcgaattgca cacccgtac gtgcttgatg ctggcattcc aatatcacaa     900
ttaacagtgt gcccacatca gtggattaat ttgaggacca caattgtgc cacaataata     960 gtgccgtaca taaacgcact acccttttgat tctgccttga accattgtaa ctttggtctg   1020
ctggttgtgc ctattagccc gttagattat gaccaaggtg cgacgccagt gatccccatt   1080
actatcactt tggccccaat gtgttttgaa tttgcaggct ttagacaagc agttacgcaa   1140
gggtttccta ctgagttgaa acctggcaca accaattttt taaccactga cgatggcgtc   1200
tcagcaccca ttctgccaaa cttttcaccc accccgtgta tccatatacc cggtgaagtt   1260
agaaacttgc tagagctatg ccaggtggag accattttag aggtcaacaa tgtacctacg   1320
aatgccacta gcttaatgga gagactgcgc ttcccggtct cagctcaagc cgggaaaggt   1380
gagctatgtg cagtgttcag agctgaccct ggacgaagtg ggccatggca gtccaccttg   1440
ttgggccagt tgtgcgggta ctacacccaa tggtcaggat cactggaagt caccttcatg   1500
ttcaccgggt cctttatggc taccggcaag atgctcatag catacacacc accaggaggc   1560
cccttaccca aggaccgggc gaccgccatg ttgggcacgg acgtcatctg ggactttggg   1620
ctgcaatcgt ctgtcactct tgtaatacca tggatcagca cactcatta cagagcgcac   1680 gctcgagatg tgtgtttga ctactacact acaggttttgg ttagcatatg gtaccagacg    1740
aattatgtgg ttccaattgg agcacccaat acagcctata taatagcatt ggcggcagcc   1800
cagaagaact tcaccatgaa gttgtgtaag gatgctagtg atatcctaca dacaggcact   1860
atccagggag ataggggtggc agatgtgatt gagagttcta taggggacag cgtgagcaga   1920
gccctcaccc gagctctacc ggcacctacc ggccaagaca cacaggtaag cagccatcga   1980
ttagatactg gtaaaggtcc agcactccaa gccgctgaaa ttggagcatc atcaaatgct   2040
agtgatgaga gtatgattga dacacggtgt gttcttaatt cacatagcac agctgagacc   2100
actcttgata gcttcttcag cagagcagga ttagttggag agatagacct ccctcttgaa   2160
ggcacaacca cccgaatgg gtacgcaaac tgggacatag acataacagg ttacgcgcaa   2220
atgcgtagaa aggtggagct gttcacctac atgcgtttta acgcagagat caccttttgtt  2280 gcatgcaccc ctaccgggga agttgtcccg caattgctcc aatatatgtt tgtaccaccc   2340
ggagccccca agccagactc cagagaatct ctcgcatggc aaactgccac taatccctcg   2400 gttttttgtga agctgtcaga ccccccagca caggtttctg ttccattcat gtcacctgcg  2460
agcgcctatc aatggttttta tgacgggtat cccacattcg gtgaacacaa acaggagaaa   2520
gaccttgaat acggggcatg cccaaacaac atgatgggta cgttctcagt gcggactgta   2580
ggcacctcga gtccaagtg cccattggtg atcaggattt acatgaggat gaagcacgtc   2640
agggcgtgga tacctcgccc aatgcgtaac cagaactatc tattcaaagc caacccaaat   2700
tatgctggta attctattaa accaactggt gccagtcgca cagcaatgaa ttctgcatct   2760
```

```
agggcggcca attccgcccc tctccctccc cccccccctaa cgttactggc cgaagccgct    2820
tggaataagg ccggtgtgcg tttgtctata tgtgattttc caccatattg ccgtcttttg    2880
gcaatgtgag ggcccggaaa cctggccctg tcttcttgac gagcattcct aggggtcttt    2940
cccctctcgc caaaggaatg caaggtctgt tgaatgtcgt gaaggaagca gttcctctgg    3000
aagcttcttg aagacaaaca acgtctgtag cgaccctttg caggcagcgg aaccccccac    3060
ctggcgacag gtgcctctgc ggccaaaagc cacgtgtata agatacacct gcaaaggcgg    3120
cacaacccca gtgccacgtt gtgagttgga tagttgtgga aagagtcaaa tggctctcct    3180
caagcgtatt caacaagggg ctgaaggatg cccagaaggt accccattgt atgggatctg    3240
atctggggcc tcggtgcaca tgctttacat gtgtttagtc gaggttaaaa aaacgtctag    3300
gccccccgaa ccacggggac gtggttttcc tttgaaaaac acgatgataa gcttgccagc    3360
ggccgcgggc cgagcttgga cttcgcccta tctctactta ggaggaacat taggcaggtc    3420
caaaccgacc agggccactt tacaatgtta ggagtgcgag accgcttggc tgtgctcccc    3480
agacactccc aaccaggaaa gaccatctgg gttgaacaca aattagtgaa gatcgtagat    3540
gctgtggagt tagtagacga acaaggggtt aacttagagc tcacactggt aacgcttgat    3600
actaacgaaa aatttagaga catcacaaga ttcataccag aaacaattag tcctgctagt    3660
gatgccactt tagttataaa tactgaacat atgcccagta tgtttgtgcc agttggagat    3720
gtggtccagt atgggttttt gaaccttagt ggtaagccca ctcacaggac tatgatgtac    3780
aatttcccaa caaaagcagg acagtgtggt ggtgttgtga ctgccgtggg taaagtgatt    3840
gggatccaca ttggtggcaa cggtagacaa ggtttctgcg ctgccctgaa gaggggatac    3900
ttttgcagtg aacaaggtga gatccaatgg atgaagccca caaagaaac tggcaggttg    3960 aacatcaacg gacctactcg cactaagctt gaaccaagtg tctttcacga tgtgttcgaa    4020
ggcactaaag agccagcagt gctgactagt aaagacccaa ggctggaagt tgactttgaa    4080
caggctcttt tttcaaaata cgtggggaac acgcttcatg aacccgacga gtttgtcaag    4140
gaggcggccc tacattatgc caaccaactc aagcagttag atatcaagac caccaagatg    4200
agcatggagg atgcatgtta cggcacagag aacctggaag ctatagatct tcacacaagt    4260
gcaggatatc catacagtgc actaggcatc aagaaaaagg acattttgga tccaacaact    4320
cgcgatgtca gcaagatgaa attctacatg acaagtatg ggttggatct accgtactct    4380
acttatgtta aagatgaact tagggccatc gacaagatca agaaagggaa gtctcgtctc    4440
atagaagcga gcagtctaaa tgactcagtg tacttgagaa tgacatttgg gcaccttat    4500 gaagctttcc acgccaatcc aggtacaatc actggttcag ctgttgggtg caacccagat    4560
gtgttctgga gcaagttacc aattctactt tcaggatcgc ttttcgcgtt tgactactcg    4620
gggtatgacg ctagtctcag cccagtgtgg ttcagggcgc tggagatagt cctgcgggaa    4680
attggatact ccgaagacgc agtgtctctc atagaaggga tcaatcacac ccatcatgtg    4740
taccgcaata aaacttattg tgttcttggg ggaatgcct caggttgctc aggcacctcc    4800
attttcaact cgatgatcaa caatatcatt attagaacac tcctgattaa acattcaaa    4860 gggatagatc taaatgaact gaacatggtg gcctacgggg atgatgtgtt ggctagttac    4920
cccttcccaa ttgactgtct ggagttggca agaacaggca aggagtatgg tctaactatg    4980 accccctgccg acaagtcacc ctgctttaat gaggttacgt gggagaatgc cactttcttg    5040
aagagaggat tcttgcctga ttatcaattc ccgtttctca tccacccac gatgccaatg    5100 agggagattc acgaatccat tcgttggacc aaagatgcac gaagtactca agatcacgtg    5160
```

```
cgctccctct gcttattagc atggctcaac gggaaagagg agtatgaaaa atttgtgagt    5220
gcaatcagat cagttccaat tggaaaagca ttggctatac caaattatga gaatctgagg    5280
agaaattggc tcgaattgtt tt                                             5302

<210> SEQ ID NO 4
<211> LENGTH: 5883
<212> TYPE: DNA
<213> ORGANISM: Artificial Sequence
<220> FEATURE:
<223> OTHER INFORMATION: expression cassette

<400> SEQUENCE: 4
ttgacgcaaa tgggcggtag gcgtgtacgg tgggaggtct atataagcag agctctctgg      60
ctaactagag aacccactgc ttactggctt atcgaaatta atacgactca ctatagggag     120
acccaagctg gctagttaag ctatcaacaa gtttgtacaa aaaagcaggc tatgggctca     180
caggtgtcca cacagcgctc cggttcgcac gaaaactcta actcagctac cgagggttcc     240
actataaact atactaccat taattactat aaagattcct atgccgccac agcaggtaag     300
cagagcctta agcaggaccc agacaagttt gcaaatcctg tcaaagacat cttcactgaa     360
atggcagcgc cattaaaatc tccatctgcc gaggcatgtg gttacagcga tcgggtggca     420
caattaacta ttggcaattc taccatcact acgcaagaag cagcaaacat catagttggc     480
tatggtgagt ggccttccta ctgttcggac tctgatgcta ctgcagtgga caaaccaacg     540
cgcccagatg tttcggtgaa taggttttac acattggaca caaaattgtg ggagaaatca     600 tccaagggggg gtactggaa attcccggat gtgttaactg aaaccggggt ctttggtcaa     660
aatgcacagt ccactaccct ctatcggtca gggttctgca ttcacgtgca gtgcaatgct     720
agtaagttcc accaaggagc actcctagtc gctgtcctcc cagagtatgt cattgggaca     780
gtggcaggtg gcacagggac ggaggatagc cacccccctt ataagcagac tcaacccggt     840
gctgatggct tcgaattgca acacccgtac gtgcttgatg ctggcattcc aatatcacaa     900
ttaacagtgt gcccacatca gtggattaat ttgaggacca caattgtgc cacaataata     960 gtgccgtaca taaacgcact acccttttgat tctgccttga accattgtaa ctttggtctg    1020
ctggttgtgc ctattagccc gttagattat gaccaaggtg cgacgccagt gatccccatt    1080
actatcactt tggccccaat gtgttttgaa tttgcaggct ttagacaagc agttacgcaa    1140
gggtttccta ctgagttgaa acctggcaca aaccaatttt taaccactga cgatggcgtc    1200
tcagcaccca ttctgccaaa cttttcaccccc acccgtgta tccatatacc cggtgaagtt    1260
agaaacttgc tagagctatg ccaggtggag accatttttag aggtcaacaa tgtacctacg    1320
aatgccacta gcttaatgga gagactgcgc ttcccggtct cagctcaagc cgggaaaggt    1380
gagctatgtg cagtgttcag agctgaccct ggacgaagtg ggccatggca gtccaccttg    1440
ttgggccagt tgtgcgggta ctacacccaa tggtcaggat cactgaagt cacccttcatg    1500 ttcaccgggt cctttatggc taccggcaag atgctcatag catacacacc accaggaggc    1560
cccttaccca aggaccgggc gaccgccatg ttgggcacgg acgtcatctg ggacttcggg    1620
ctgcaatcgt ctgtcactct tgtaatacca tggatcagca cactcattaa cagagcgcac    1680
gctcgagatg gtgtgtttga ctactacact acaggtttgg ttagcatatg gtaccagacg    1740
aattatgtgg ttccaattgg agcacccaat acagcctata ataagcatt ggcggcagcc    1800 cagaagaact tcaccatgaa gttgtgtaag gatgctagta tatcctaca gacaggcact    1860 atccagggag ataggtggc agatgtgatt gagagttcta taggggacag cgtgagcaga    1920
```

```
gccctcaccc gagctctacc ggcacctacc ggccaagaca cacaggtaag cagccatcga    1980
ttagatactg gtaaaggtcc agcactccaa gccgctgaaa ttggagcatc atcaaatgct    2040
agtgatgaga gtatgattga gacacggtgt gttcttaatt cacatagcac agctgagacc    2100
actcttgata gcttcttcag cagagcagga ttagttggag agatagacct ccctcttgaa    2160
ggcacaacca acccgaatgg gtacgcaaac tgggacatag acataacagg ttacgcgcaa    2220
atgcgtagaa aggtggagct gttcacctac atgcgtttta acgcagagat cacctttgtt    2280
gcatgcaccc ctaccgggga agttgtcccg caattgctcc aatatatgtt tgtaccaccc    2340
ggagccccca agccagactc cagagaatct ctcgcatggc aaaactgcca c taatccctcg    2400 gtttttgtga agctgtcaga cccccagca caggtttctg ttccattcat gtcacctgcg     2460
agcgcctatc aatggtttta tgacgggtat cccacattcg gtgaacacaa acaggagaaa    2520
gaccttgaat acggggcatg cccaaacaac atgatgggta cgttctcagt gcggactgta    2580
ggcacctcga gtccaagtg cccattggtg atcaggattt acatgaggat gaagcacgtc     2640
agggcgtgga tacctcgccc aatgcgtaac cagaactatc tattcaaagc caacccaaat    2700
tatgctggta attctattaa accaactggt gccagtcgca cagcaatgaa ttcgtgaggc    2760
tccggtgccc gtcagtgggc agagcgcaca tcgcccacag tccccgagaa gttgggggga    2820
ggggtcggca attgaaccgg tgcctagaga aggtggcgcg gggtaaactg ggaaagtgat    2880
gtcgtgtact ggctccgcct ttttcccgag ggtgggggag aaccgtatat aagtgcagta    2940
gtcgccgtga acgttctttt tcgcaacggg tttgccgcca gaacacaggt aagtgccgtg    3000
tgtggttccc gcgggcctgg cctctttacg ggttatggcc cttgcgtgcc ttgaattact    3060
tccacctggc tgcagtacgt gattcttgat cccgagcttc gggttggaag tgggtgggag    3120
agttcgaggc cttgcgctta aggagcccct tcgcctcgtg cttgagttga ggcctggcct    3180
gggcgctggg gccgccgcgt gcgaatctgg tggcaccttc gcgcctgtct cgctgctttc    3240
gataagtctc tagccattta aaatttttga tgacctgctg cgacgctttt tttctggcaa    3300
gatagtcttg taaatgcggg ccaagatctg cacactggta tttcggtttt tggggtcgcg    3360
ggcggcgacg gggcccgtgc gtcccagcgc acatgttcgg cgaggcgggg cctgcgagcg    3420
cggccaccga gaatcggacg ggggtagtct caagctggcc ggcctgctct ggtgcctggc    3480
ctcgcgccgc cgtgtatcgc cccgccctgg gcggcaaggc tggcccggtc ggcaccagtt    3540
gcgtgagcgg aaagatggcc gcttcccggc cctgctgcag ggagctcaaa atggaggacg    3600
cggcgctcgg gagagcgggc gggtgagtca cccacacaaa ggaaaagggc ctttccgtcc    3660
tcagccgtcg cttcatgtga ctccacggag taccgggcgc cgtccaggca cctcgattag    3720
ttctcgagct tttggagtac gtcgtcttta ggttggggg aggggtttta tgcgatggag     3780 tttcccaca ctgagtgggt ggagactgaa gttaggccag cttggcactt gatgtaattc     3840
tccttggaat ttgcccttt tgagtttgga tcttggttca ttctcaagcc tcagacagtg     3900
gttcaaagtt tttttcttcc atttcaggtg tcgtgaaaag cggccgcggg ccgagcttgg    3960
acttcgccct atctctactt aggaggaaca ttaggcaggt ccaaaccgac cagggccact    4020
ttacaatgtt aggagtgcga gaccgcttgg ctgtgctccc cagacactcc caaccaggaa    4080
agaccatctg ggttgaacac aaattagtga agatcgtaga tgctgtggag ttagtagacg    4140 aacaagggt taacttagag ctcacactgg taacgcttga tactaacgaa aaatttagag     4200
acatcacaag attcatacca gaaacaatta gtcctgctag tgatgccact ttagttataa    4260
atactgaaca tatgcccagt atgtttgtgc cagttggaga tgtggtccag tatgggtttt    4320
```

-continued

```
tgaaccttag tggtaagccc actcacagga ctatgatgta caatttccca acaaaagcag    4380
gacagtgtgg tggtgttgtg actgccgtgg gtaaagtgat tgggatccac attggtggca    4440
acggtagaca aggtttctgc gctgccctga gaggggata cttttgcagt gaacaaggtg     4500
agatccaatg gatgaagccc aacaaagaaa ctggcaggtt gaacatcaac ggacctactc    4560
gcactaagct tgaaccaagt gtctttcacg atgtgttcga aggcactaaa gagccagcag    4620
tgctgactag taaagaccca aggctggaag ttgactttga acaggctctt ttttcaaaat    4680
acgtggggaa cacgcttcat gaacccgacg agtttgtcaa ggaggcggcc ctacattatg    4740
ccaaccaact caagcagtta gatatcaaga ccaccaagat gagcatggag gatgcatgtt    4800
acggcacaga gaacctggaa gctatagatc ttcacacaag tgcaggatat ccatacagtg    4860
cactaggcat caagaaaaag gacattttgg atccaacaac tcgcgatgtc agcaagatga    4920
aattctacat ggacaagtat gggttggatc taccgtactc tacttatgtt aaagatgaac    4980
ttagggccat cgacaagatc aagaaaggga agtctcgtct catagaagcg agcagtctaa    5040
atgactcagt gtacttgaga atgacatttg gcacccttta tgaagctttc cacgccaatc    5100
caggtacaat cactggttca gctgttgggt gcaacccaga tgtgttctgg agcaagttac    5160
caattctact ttcaggatcg cttttcgcgt ttgactactc ggggtatgac gctagtctca    5220
gcccagtgtg gttcagggcg ctggagatag tcctgcggga aattggatac tccgaagacg    5280
cagtgtctct catagaaggg atcaatcaca cccatcatgt gtaccgcaat aaaacttatt    5340
gtgttcttgg gggaatgccc tcaggttgct caggcacctc catttcaac tcgatgatca     5400 acaatatcat tattagaaca ctcctgatta aacattcaa agggatagat ctaaatgaac      5460
tgaacatggt ggcctacggg gatgatgtgt tggctagtta ccccttccca attgactgtc    5520
tggagttggc aagaacaggc aaggagtatg gtctaactat gaccccctgcc gacaagtcac   5580 cctgctttaa tgaggttacg tgggagaatg ccactttctt gaagagagga ttcttgcctg    5640
attatcaatt cccgtttctc atccacccta cgatgccaat gagggagatt cacgaatcca    5700
ttcgttggac caaagatgca cgaagtactc aagatcacgt gcgctcccte tgcttattag    5760 catggctcaa cgggaaagag gagtatgaaa aatttgtgag tgcaatcaga tcagttccaa    5820
ttggaaaagc attggctata ccaaattatg agaatctgag gagaaattgg ctcgaattgt    5880
ttt                                                                  5883
```

<210> SEQ ID NO 5
<211> LENGTH: 183
<212> TYPE: PRT
<213> ORGANISM: Enterovirus 71

<400> SEQUENCE: 5

```
Gly Pro Ser Leu Asp Phe Ala Leu Ser Leu Leu Arg Arg Asn Ile Arg
1               5                   10                  15

Gln Val Gln Thr Asp Gln Gly His Phe Thr Met Leu Gly Val Arg Asp
            20                  25                  30

Arg Leu Ala Val Leu Pro Arg His Ser Gln Pro Gly Lys Thr Ile Trp
        35                  40                  45

Val Glu His Lys Leu Val Lys Ile Val Asp Ala Val Glu Leu Val Asp
    50                  55                  60

Glu Gln Gly Val Asn Leu Glu Leu Thr Leu Val Thr Leu Asp Thr Asn
65                  70                  75                  80

Glu Lys Phe Arg Asp Ile Thr Arg Phe Ile Pro Glu Thr Ile Ser Pro
                85                  90                  95
```

Ala Ser Asp Ala Thr Leu Val Ile Asn Thr Glu His Met Pro Ser Met
            100                 105                 110

Phe Val Pro Val Gly Asp Val Val Gln Tyr Gly Phe Leu Asn Leu Ser
        115                 120                 125

Gly Lys Pro Thr His Arg Thr Met Met Tyr Asn Phe Pro Thr Lys Ala
    130                 135                 140

Gly Gln Cys Gly Gly Val Val Thr Ala Val Gly Lys Val Ile Gly Ile
145                 150                 155                 160

His Ile Gly Gly Asn Gly Arg Gln Gly Phe Cys Ala Ala Leu Lys Arg
                165                 170                 175

Gly Tyr Phe Cys Ser Glu Gln
                180

<210> SEQ ID NO 6
<211> LENGTH: 462
<212> TYPE: PRT
<213> ORGANISM: Enterovirus 71

<400> SEQUENCE: 6

Gly Glu Ile Gln Trp Met Lys Pro Asn Lys Glu Thr Gly Arg Leu Asn
1               5                   10                  15

Ile Asn Gly Pro Thr Arg Thr Lys Leu Glu Pro Ser Val Phe His Asp
            20                  25                  30

Val Phe Glu Gly Thr Lys Glu Pro Ala Val Leu Thr Ser Lys Asp Pro
        35                  40                  45

Arg Leu Glu Val Asp Phe Glu Gln Ala Leu Phe Ser Lys Tyr Val Gly
    50                  55                  60

Asn Thr Leu His Glu Pro Asp Glu Phe Val Lys Glu Ala Ala Leu His
65                  70                  75                  80

Tyr Ala Asn Gln Leu Lys Gln Leu Asp Ile Lys Thr Thr Lys Met Ser
                85                  90                  95

Met Glu Asp Ala Cys Tyr Gly Thr Glu Asn Leu Glu Ala Ile Asp Leu
            100                 105                 110

His Thr Ser Ala Gly Tyr Pro Tyr Ser Ala Leu Gly Ile Lys Lys Lys
        115                 120                 125

Asp Ile Leu Asp Pro Thr Thr Arg Asp Val Ser Lys Met Lys Phe Tyr
    130                 135                 140

Met Asp Lys Tyr Gly Leu Asp Leu Pro Tyr Ser Thr Tyr Val Lys Asp
145                 150                 155                 160

Glu Leu Arg Ala Ile Asp Lys Ile Lys Lys Gly Lys Ser Arg Leu Ile
                165                 170                 175

Glu Ala Ser Ser Leu Asn Asp Ser Val Tyr Leu Arg Met Thr Phe Gly
            180                 185                 190

His Leu Tyr Glu Ala Phe His Ala Asn Pro Gly Thr Ile Thr Gly Ser
        195                 200                 205

Ala Val Gly Cys Asn Pro Asp Val Phe Trp Ser Lys Leu Pro Ile Leu
    210                 215                 220

Leu Ser Gly Ser Leu Phe Ala Phe Asp Tyr Ser Gly Tyr Asp Ala Ser
225                 230                 235                 240

Leu Ser Pro Val Trp Phe Arg Ala Leu Glu Ile Val Leu Arg Glu Ile
                245                 250                 255

Gly Tyr Ser Glu Asp Ala Val Ser Leu Ile Glu Gly Ile Asn His Thr
            260                 265                 270

His His Val Tyr Arg Asn Lys Thr Tyr Cys Val Leu Gly Gly Met Pro
        275                 280                 285

-continued

```
Ser Gly Cys Ser Gly Thr Ser Ile Phe Asn Ser Met Ile Asn Asn Ile
290                 295                 300

Ile Ile Arg Thr Leu Leu Ile Lys Thr Phe Lys Gly Ile Asp Leu Asn
305                 310                 315                 320

Glu Leu Asn Met Val Ala Tyr Gly Asp Asp Val Leu Ala Ser Tyr Pro
            325                 330                 335

Phe Pro Ile Asp Cys Leu Glu Leu Ala Arg Thr Gly Lys Glu Tyr Gly
            340                 345                 350

Leu Thr Met Thr Pro Ala Asp Lys Ser Pro Cys Phe Asn Glu Val Thr
        355                 360                 365

Trp Glu Asn Ala Thr Phe Leu Lys Arg Gly Phe Leu Pro Asp Tyr Gln
370                 375                 380

Phe Pro Phe Leu Ile His Pro Thr Met Pro Met Arg Glu Ile His Glu
385                 390                 395                 400

Ser Ile Arg Trp Thr Lys Asp Ala Arg Ser Thr Gln Asp His Val Arg
            405                 410                 415

Ser Leu Cys Leu Leu Ala Trp Leu Asn Gly Lys Glu Glu Tyr Glu Lys
            420                 425                 430

Phe Val Ser Ala Ile Arg Ser Val Pro Ile Gly Lys Ala Leu Ala Ile
        435                 440                 445

Pro Asn Tyr Glu Asn Leu Arg Arg Asn Trp Leu Glu Leu Phe
450                 455                 460

<210> SEQ ID NO 7
<211> LENGTH: 22
<212> TYPE: DNA
<213> ORGANISM: Artificial Sequence
<220> FEATURE:
<223> OTHER INFORMATION: Primer F (VP1)

<400> SEQUENCE: 7
acgcgcaaat gcgtagaaag gt                                          22

<210> SEQ ID NO 8
<211> LENGTH: 22
<212> TYPE: DNA
<213> ORGANISM: Artificial Sequence
<220> FEATURE:
<223> OTHER INFORMATION: Primer R (VP1)

<400> SEQUENCE: 8
ttagtggcag tttgccatgc ga                                          22

<210> SEQ ID NO 9
<211> LENGTH: 24
<212> TYPE: DNA
<213> ORGANISM: Artificial Sequence
<220> FEATURE:
<223> OTHER INFORMATION: Primer F (b-actin)

<400> SEQUENCE: 9
accaactggg acgacatgga gaaa                                        24

<210> SEQ ID NO 10
<211> LENGTH: 24
<212> TYPE: DNA
<213> ORGANISM: Artificial Sequence
<220> FEATURE:
<223> OTHER INFORMATION: Primer R (b-actin)
```

```
<400> SEQUENCE: 10
tagcacagcc tggatagcaa cgta                                          24

<210> SEQ ID NO 11
<211> LENGTH: 30
<212> TYPE: DNA
<213> ORGANISM: Artificial Sequence
<220> FEATURE:
<223> OTHER INFORMATION: Primer F (P1)

<400> SEQUENCE: 11
atcggaattc atgggctcac aggtgtccac                                    30

<210> SEQ ID NO 12
<211> LENGTH: 29
<212> TYPE: DNA
<213> ORGANISM: Artificial Sequence
<220> FEATURE:
<223> OTHER INFORMATION: Primer R (P1)

<400> SEQUENCE: 12
cttgtcgact tagagagtgg taattgctg                                     29

<210> SEQ ID NO 13
<211> LENGTH: 28
<212> TYPE: DNA
<213> ORGANISM: Artificial Sequence
<220> FEATURE:
<223> OTHER INFORMATION: Primer F (3CD)

<400> SEQUENCE: 13
atcggaattc atggggccga gcttggac                                      28

<210> SEQ ID NO 14
<211> LENGTH: 24
<212> TYPE: DNA
<213> ORGANISM: Artificial Sequence
<220> FEATURE:
<223> OTHER INFORMATION: Primer R (3CD)

<400> SEQUENCE: 14
atcgctcgag aaacaattcg agcc                                          24

<210> SEQ ID NO 15
<211> LENGTH: 27
<212> TYPE: DNA
<213> ORGANISM: Artificial Sequence
<220> FEATURE:
<223> OTHER INFORMATION: Primer F (EF-1a)

<400> SEQUENCE: 15
atcgacgcgt gtgaggctcc ggtgccc                                       27

<210> SEQ ID NO 16
<211> LENGTH: 26
<212> TYPE: DNA
<213> ORGANISM: Artificial Sequence
<220> FEATURE:
<223> OTHER INFORMATION: Primer R (EF-1a)

<400> SEQUENCE: 16
atcgcccggg gttttcacga cacctg                                        26
```

ADENOVIRAL VECTOR-BASED VACCINE AGAINST ENTEROVIRUS INFECTION

RELATED APPLICATION

This application is a national stage filing under 35 U.S.C. § 371 of international PCT application PCT/US2015/022738, filed Mar. 26, 2015, which claims the benefit of U.S. Provisional Patent Application No. 61/985,803, filed Apr. 29, 2014 under 35 U.S.C. § 119(e), the content of each of which is herein incorporated by reference in its entirety.

TECHNOLOGY FIELD

The present invention relates in general to the field of immunization, and particularly, an adenoviral vector-based vaccine against enterovirus infection.

BACKGROUND OF THE INVENTION

Enteroviruses, within the Picornaviridae family, are a genus of small, non-enveloped viruses containing positive-strand RNAs. The *Enterovirus* genus now comprises 12 species: *Enterovirus A, Enterovirus B, Enterovirus C, Enterovirus D, Enterovirus E, Enterovirus F, Enterovirus G, Enterovirus H, Enterovirus J, Rhinovirus A, Rhinovirus B* and *Rhinovirus C*. These viruses infect the intestinal tract but can cause various types of diseases. Typical enterovirus diseases are meningitis, paralysis, myocarditis, hand, foot and mouth-disease (HFMD), herpangina, pleurodynia, hepatitis, rash and respiratory diseases including pneumonia. The only enterovirus vaccine for use in human beings is vaccine of poliovirus which belongs to *Enterovirus C*. Currently, vaccines against non-polio enteroviruses are not available for human use.

Among *Enterovirus A*, enterovirus 71 (EV71) and coxsackievirus A group (CVA) infections are the most common causative factors of hand, foot, and mouth disease (HFMD) and other neurological disorders. Severe neurological disorders, including encephalitis, acute flaccid paralysis, pulmonary edema (PE), and hemorrhaging, culminating in fatality, particularly in EV71-infected children under 5 years old, have been reported [1-5]. Because EV71 and CVA infections can potentially become a new threat to global public health [1, 6-11], effective antiviral drugs and prophylactic vaccines are urgently needed.

Enterovirus genome consists of a single open reading frame that encodes the P1, P2, and P3 poly-proteins. The P2 and P3 regions encode nonstructural proteins (e.g., 3CD) responsible for virus replication and virulence. During viral RNA translation, the 2A protein catalyzes its N-terminal cleavage in cis, thereby releasing the capsid proteins in the P1 region from the nascent nonstructural proteins in the P2 and P3 regions. 3CD is released from the P3 precursor by autocatalytic cleavage. A 3C' cleavage site in the polyprotein resides between the 3C and 3D portion of 3CD to generate 2 products, 3C' and 3D'. When the P1 precursor is encoded by the P1 region, it can be cleaved by the 3C' protease into VP0, VP1, and VP3. These 3 proteins spontaneously assemble into an icosahedral procapsid and pack the RNA genome into the provirion that could be a non-infectious empty (E)-particle or infectious full (F)-particle [12,13].

Human scavenger receptor class B, member 2 (hSCARB2) and human P-selectin glycoprotein ligand 1 (PSGL-1) have been identified as the important cell receptors for EV71 infection [14,15]. Our group [16] and Fujii et al. [17] have successfully developed transgenic mice expressing the human hSCARB2 receptor. In this promising model, transgenic animals infected with clinical EV71 isolates of the B4 and B5 subgenotypes developed HFMD-like skin rashes, whereas those inoculated with EV71 C2 and C4 subgenotypes or CVA16 suffered severe limb paralysis and death. In addition, passive administration of the monoclonal anti-EV71 VP1 neutralizing antibody N3 [26] reduced EV71 B5 infection-induced symptoms and protected the transgenic mice against EV71 C2-induced severe limb paralysis and death.

In a previous study [13], we produced a formalin-inactivated EV71 strain E59 (FI-EV71) vaccine candidate formulated with alum adjuvant, and found that FI-EV71 displayed high efficacy in the hSCARB2-Tg mouse challenge model [16]. In a human phase I clinical trial [18], FI-EV71 was safe and could elicit strong neutralizing antibody responses against current circulating EV71 isolates, but failed to protect against CVA16 infections. On the other hand, DNA vaccine (100 μg/mouse) and recombinant protein vaccine (10 μg/mouse) based on VP1, the most potent antigen on the EV71 virus, induce poorer immune responses than the inactivated virus vaccines and fail to effectively protect the mice against virus infection [19].

Virus-like particles, or VLPs, mimic the external protein structure of a virus without including the genetic material (DNA or RNA) that is necessary for viral replication. Without genetic material, VLP vaccines are incapable of causing infections themselves while at the same time presenting viral antigens in the most authentic configuration possible. VLPs of EV71 produced by insect cells also had been proved its efficacy in mice [20], which describes that VLP proteins are expressed in insect cells and then resemble to form VLPs and after purification, the VLPs are introduced to mice for immunization, inducing immune responses against the viral challenge. However, the different post-modification (such as glycosylation) of VLPs proteins produced from non-human cells might induce the different immunogenicity from human. The highest purity demand of VLPs during the production is also an obstacle.

There is still a need to develop an effective vaccine against enterovirus infections.

BRIEF SUMMARY OF THE INVENTION

The present invention relates to a novel adenoviral vector-based DNA vaccine for generating immunity against enterovirus infection. In one embodiment, the present invention provides a recombinant adenoviral vector which comprises an expression cassette encoding a P1 protein and a 3CD protease of an enterovirus. In another embodiment, the present invention provides a recombinant adenoviral vector which comprises an expression cassette encoding a 3C protease or a 3CD protease of an enterovirus. It is unexpectedly found that vaccination of the recombinant adenoviral vector as described induces enhanced protective immunity against enterovirus infection, especially cellular (T cell) immune responses. It is also found that vaccination of the recombinant adenoviral vector as described induces specific 3C cellular immune responses and thus provides broad cross-protection against different species of enteroviruses, including at least enterovirus 71 and coxsackievirus A, because the amino acid sequences of the 3C protease among the enteroviruses are highly conserved.

Therefore, in one aspect, the present invention provides a recombinant adenoviral vector for generating immunity against enterovirus infection comprising an expression cassette encoding a P1 protein and a 3CD protease of an enterovirus. The present invention also provides a recombinant adenoviral vector for generating immunity against enterovirus infection comprising an expression cassette encoding a 3C protease or a 3CD protease of an enterovirus.

In another aspect, the present invention provides a vaccine composition for generating immunity against enterovirus infection comprising an effective amount of the recombinant adenoviral vector as described herein.

In a further aspect, the present invention provides a method of inducing an immune response in a subject against enterovirus infection, comprising administering to the subject an effective amount of the recombinant adenoviral vector or the vaccine composition as described herein. Also provided is use of the recombinant adenoviral vector or the vaccine composition as described herein for manufacturing a medicament (e.g. a vaccine) for inducing an immune response in a subject against enterovirus infection.

In addition, it is found that virus-like particles are formed in a mammalian cell expression system using the recombinant adenoviral vector of the invention encoding P1 and 3CD proteins. Therefore, the present invention further provides a method for producing virus like particles of an enterovirus, comprising culturing mammalian cells transfected with a recombinant adenoviral vector as described herein under conditions that allow the expression of the P1 protein and the 3CD protease and assembly of the virus like particles of the enterovirus; and collecting the cultured mammalian cells and isolating the virus like particles of the enterovirus therefrom.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 14 shows the nucleotide sequence of CMP promoter-P1 gene-IRES-3CD gene cassette in one embodiment of the invention (SEQ ID NO: 3).

FIG. 15 shows the nucleotide sequence of CMP promoter-P1 gene-EF-1α promoter-3CD gene cassette in one embodiment of the invention (SEQ ID NO: 4).

FIG. 16 shows the sequence information of the 3C protease, 3C protease and 3CD protease of EV71.

FIG. 17 shows the sequence information of the P1 protein of EV71.

DETAILED DESCRIPTION OF THE INVENTION

Figure 1:
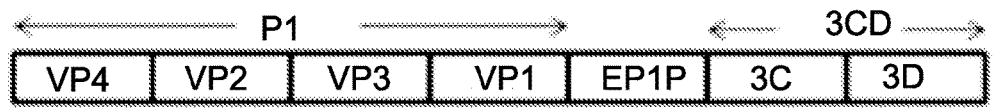
FIG. 1 shows construction of a recombinant adenovirus vector carrying EV71 P1 and 3CD genes and expressing VLPs. (A) Adenovirus construct; Ad-EVVLP expresses the P1 gene, which is comprised of VP1 to VP4 subunit sequences driven by the CMV promoter and the 3CD gene driven by elongation factor-1α promoter (EF1p). (B) Specific primers against the P1, 3CD, and EF1p sequences were used to amplify and detect the insertion of P1, 3CD, and the EF-1α promoter in the Ad-EVVLP construct. (C) Ad-LacZ and Ad-EVVLP produced from the lysates of 293A transfectants were analyzed by immunoblotting with the polyclonal anti-Ad5 antibody. The cascade of VLP formation is shown; the translated P1 polypeptide was produ region of EV71 RNA. Quantitative RT-PCR using primers specific to the β-Actin gene was used as the internal control. Relative VP1 mRNA expression in the individual Ad-EV-VLP-vaccinated tissues was normalized to β-actin expression in each individual sample and then to the mean of relative normalized VP1 mRNA expression in Ad-LacZ-vaccinated samples. The mean relative expression in each group of 7 mice was calculated. Unpaired student's t-tests with Welch corrections were used for statistical analysis.
Figure 1:
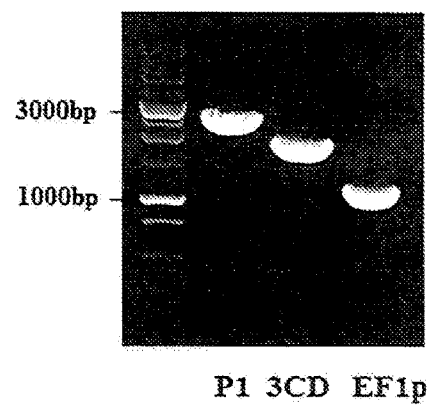

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, the phrase "a gene encoding a protein" means that transcription and translation of mRNA produced by that gene can produce the protein in a cell or other biological system. It is understood by a skilled person that numerous different polynucleotides can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant" nucleic acid refers to a polynucleotide or nucleic acid molecule having sequences that are not naturally joined together. A recombinant nucleic acid may be present in the form of a construct e.g. a vector. "Vectors" may contain a given nucleotide sequence of interest and a regulatory sequence. Vectors may be used for expressing the given nucleotide sequence or maintaining the given nucleotide sequence for replicating it, manipulating it or transferring it between different locations (e.g., between different organisms). Vectors can be introduced into a suitable host cell for the above mentioned purposes.

As used herein, the term "operably linked" may mean that a polynucleotide is linked to an expression control sequence in such a manner to enable expression of the polynucleotide when a proper molecule (such as a transcriptional factor) is bound to the expression control sequence.

As used herein, the term "expression control sequence" or "regulatory sequence" means a DNA sequence that regulates expression of the nucleic acid sequence operably linked thereto in a certain host cell.

As used herein, the term "expression cassette" refers to a defined segment of a nucleic acid molecule that comprises the minimum elements needed for production of a transcriptional or translational product (RNA or protein) encoded by that nucleic acid molecule. For example, an expression cassette includes a polynucleotide sequence encoding a polypeptide to be expressed and sequences for controlling its expression such as a promoter and optionally an enhancer sequence, including any combination of cis-acting transcriptional control elements. For an adenoviral vector as described herein, an expression cassette can typically refer to that for expressing a heterologous gene product, rather than that for expressing adenoviral proteins encoded in the adenoviral genome.

Typically, in vectors, a given nucleotide sequence is operatively linked to a regulatory sequence, forming an expression cassette, such that when the vectors are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, alcohol oxidase gene (AOX1) promoter, internal ribosome entry site (IRES) and elongation factor 1a promoter), a start codon, a replication origin, enhancers, an operator sequence, a secretion signal sequence (e.g., α-mating factor signal) and other control sequence (e.g., Shine-Dalgano sequences and termination sequences). Preferably, vectors may further contain a marker sequence (e.g., an antibiotic resistant marker sequence) for the subsequent screening procedure.

The term "vaccine" refers to an agent or composition containing an active component effective to induce protective immunity in a subject against a certain pathogen or disease. Traditionally, the active component of a vaccine is a polypeptide derived from a pathogen which is the target of the vaccine. The term "DNA vaccine" refers to a vaccine wherein the active component is composed of DNAs e.g. a DNA construct expressing a desired antigenic protein to induce protective immune responses. As described herein, a DNA vaccine can refer to a DNA construct for expressing viral proteins or VLPs of a virus and induce protective immune responses against the virus in a subject after vaccination.

A "subject" as used herein is a human or non-human mammal. Non-human mammals include, but are not limited to, primates, ungulates, canines and felines.

The term "adenovirus" as referred to herein indicates over 47 adenoviral subtypes isolated from humans, and as many from other mammals and birds. See, Strauss, "Adenovirus infections in humans," in The Adenoviruses, Ginsberg, ed., Plenum Press, New York, N.Y., pp. 451 596 (1984).

The term "adenoviral vector" as used herein refers to an adenovirus in which the adenoviral genome has been manipulated to carry a nucleic acid sequence that is non-native with respect to the adenoviral genome. Therefore, a "recombinant adenoviral vector" as used herein typically comprises an adenoviral genome and an expression cassette in which at least one exogenous nucleic acid sequence encoding a desired protein (e.g. P1 protein or 3CD protein or both) is included.

An adenoviral vector preferably contains at least a portion of each terminal repeat required to support the replication of the viral DNA, preferably at least about 90% of the full inverted terminal repeat (ITR) sequence, and the DNA required to encapsidate the genome into a viral capsid. Adenovirus from various origins can be used as the source of the viral genome for the adenoviral vector. A human adenovirus is preferred, for example, subgroup A (e.g., serotypes 12, 18 and 31), subgroup B (e.g., serotypes 3, 7, 11, 14, etc.), subgroup C (e.g., serotypes 1, 2, 5, and 6), subgroup D (e.g., serotypes 8, 9, 10, 13, 15, 17, 19, 20, etc.), subgroup E (e.g., serotype 4), subgroup F (e.g., serotypes 40 and 41) and others. Preferably, the adenoviral vector is of human subgroup C, especially serotype 2 or even more desirably serotype 5.

The adenoviral vector can be replication competent. Typically, the adenoviral vector is replication-deficient in host cells. The term "replication-defective" means that the adenoviral vector has a deficiency in one or more gene functions or regions of the adenoviral genome for replication (e.g. E1, E3 or E4 region) such that the vector keeps some low-level replication or does not replicate in normal host cells, especially those in a human to be infected by the adenoviral vector. The replication-defective adenoviral vector ensures the safety of the vaccine. In one embodiment, the adenoviral vector is deficient in E1 or E3 or both. A deficiency in a gene is defined as a mutation or deletion to completely remove or impair the function of the gene, for example, such that the function of the gene product is reduced by at least about 2-fold, 5-fold, 10-fold, 20-fold or more as compared to a native gene. The resulting replication-defective adenoviral vector can accommodate one or more exogenous nucleic acid sequences, in a proper site in the adenoviral genome, for expression of one or more desired proteins, while maintaining the ability to be packaged into adenoviral capsids. For the purpose of producing high titers of viral vector for stock, the replication-defective adenoviral vector is typically produced in complementing cell lines, such as 293 cells, which provide gene functions not present in the replication-defective adenoviral vector.

In one aspect, the present invention provides a recombinant adenoviral vector as a broad spectrum DNA vaccine for generating immunity against various enterovirus infections.

In one embodiment, the recombinant adenoviral vector of the invention comprises an expression cassette encoding a P1 protein and a 3CD protease of an enterovirus. The recombinant adenoviral vector of the invention, Ad-P1-3CD, upon transfection in host cells, not only expresses adenoviral structure proteins but also enterovirus capsid proteins, and in addition to the adenovirus particles, VLPs formed by assembly of these expressed enterovirus capsid proteins, are produced, as demonstrated in western blotting and transmission electron microscopy. Ad-P1-3CD can be used as a broad spectrum DNA vaccine for generating immunity against various enterovirus infections, especially *Enterovirus A* covering EV71 and CVA. As shown in examples below, in animals, immunization of Ad-P1-3CD can induce neutralizing antibodies against EV71 and specific cellular $CD4^{++}$ and $CD^{8+}$ cellular immunities against both EV71 and CVA; and Ad-P1-3CD provides protection against EV71 and CVA infection in animals (100% survival of mice immunized with Ad-P1-3CD after challenge with EV71 or CVA, as compared with 0% survival of mice received saline or control adenoviral vector).

To construct the recombinant adenoviral vector of the invention, the exogenous DNA can be inserted in a proper site in the adenoviral genome of the vector using standard molecular biology and cell culture techniques, such as those described in Sambrook et al., Molecular Cloning, a Laboratory Manual, $3^{rd}$ edition, Cold Spring Harbor Press, Cold Spring harbor, N.Y. (2001). When the adenoviral vector comprise two or more exogenous nucleic acid sequences for expressing proteins, the multiple nucleic acid sequences can be operably linked to different or the same promoters e.g. two nucleic acid sequences are each operably linked to the same one promoter, or each of the two nucleic acid sequences is operably linked to a different promoter. In this regard, the promoter can be a viral promoter such as a T7 promoter, a CMV promoter, a human immunodeficiency virus (HIV) long terminal repeat promoter, an internal ribosome entry site (IRES), a herpes thymidine kinase promoter or an adeno-associated viral promoter such as the p5 promoter and the like. Alternatively, the promoter can be a cellular promoter i.e. a promoter that is present in eukaryotic cells (animal cells or yeast cells), such as a ubiquitin promoter, a EF-1α promoter, a heat shock protein promoter, a β-active promoter, or an alcohol oxidase gene (AOX1) promoter.

In one certain embodiment, the recombinant adenoviral vector of the invention comprises an expression cassette including a first nucleic acid fragment encoding the P1 protein and a second nucleic acid fragment encoding the 3CD protease. Specifically, the first nucleic acid fragment is operably linked to a first promoter for controlling expression of the P1 protein and the second nucleic acid fragment is operably linked to a second promoter for controlling expression of the 3CD protease, in which the first promoter and the second promoter are the same or different. Specific examples of the expression cassette in the recombinant adenoviral vector of the invention are as shown in FIG. 14 and FIG. 15, respectively, one being a CMV promoter operably linked to a P1 gene, connected with an IRES promoter operably linked to a 3CD gene (CMV-P1-IRES-3CD); and the other being a CMV promoter operably linked to a P1 gene, connected with an EF-1α promoter operably linked to a 3CD gene (CMV-P1-EF-1α-3CD).

As used herein, a "P1 protein" is a protein product expressed by a P1 gene of an enterovirus. The amino acid sequence of the P1 protein and its corresponding nucleic acid are available in the art. In certain embodiments, the P1 protein as described herein is the one originated from EV71, particularly having the amino acid sequence of SEQ ID NO: 1, or the one from other enterovirus species having the amino acid sequence with at least 85%, 90% or 95% identity to SEQ ID NO: 1.

As used herein, a "3CD protease" is a protein product expressed by a 3CD gene of an enterovirus. The amino acid sequence of the 3CD protein and its corresponding nucleic acid are available in the art. In certain embodiments, the 3CD protein as described herein is the one originated from EV71, particularly having the amino acid sequence of SEQ ID NO: 2, or the one from other enterovirus species having the amino acid sequence with at least 85%, 90% or 95% identity to SEQ ID NO: 2.

In particular embodiments, the P1 protein and the 3CD protease are originated from the same species of an enterovirus, for example, EV71.

In certain examples, the recombinant adenoviral vector of the invention comprises an expression cassette which includes the nucleic acid sequence of SEQ ID NO: 3 (CMV-P1-IRES-3CD) or SEQ ID NO: 4 (CMV-P1-EF-1α-3CD).

In the present invention, it is also disclosed that a 3C specific cellular immunity is sufficient to protect various enterovirus infections, at least *Enterovirus A* infections, covering EV71 and CVA infections. Therefore, the present invention also provides a recombinant adenoviral vector for generating immunity against enterovirus infection comprising an expression cassette encoding a 3C protease or a 3CD protease of an enterovirus. In one embodiment, the present invention provides a recombinant adenoviral vector comprising an expression cassette carrying an exogenous DNA encoding a 3C protease of an enterovirus. In another embodiment, the present invention provides a recombinant adenoviral vector comprising an expression cassette carrying an exogenous DNA encoding a 3CD protease of an enterovirus. In a particular example, the 3C protease or the 3CD protease is originated from EV71.

As used herein, a "3C" protein is a protein product expressed by a 3C gene of an enterovirus. The amino acid sequence of the 3C protein and its corresponding nucleic acid are available in the art. In certain embodiments, the 3C protein as described herein is the one originated from EV71, particularly having the amino acid sequence of SEQ ID NO: 5, or the one from other enterovirus species having the amino acid sequence with at least 85%, 90% or 95% identity to SEQ ID NO: 5.

To determine the percent identity of two amino acid sequences, the sequences are aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

An effective amount of the recombinant adenoviral vector of the invention as the active ingredient can be formulated with a pharmaceutically acceptable carrier into a composition of an appropriate form for the purpose of delivery or absorption or to enhance stability of the composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Viral vectors may be formulated as solutions or lyophilized powders for parenteral administration. Powders may be reconstituted with a suitable diluents or other pharmaceutically acceptable carrier before use. Suitable diluents for example are normal isotonic saline solution, standard 5% dextrose in water, or buffered sodium or ammonium acetate solution. Viral vectors may be prepared for oral administration. Some examples of appropriate solid carriers include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to a subject.

The composition of the present invention comprising the recombinant adenoviral vector of the invention, as a vaccine composition, can further formulated to comprise an adjuvant. Typical examples of adjuvants to enhance effectiveness of a vaccine composition include, but are not limited to, aluminum salts, oil-in-water emulsion formulations, saponin adjuvants, complete Freund's adjuvant (CFA) and incomplete Freund's adjuvant (IFA).

The present invention further provides a method of inducing an immune response in a subject against enterovirus infection, comprising administering to the subject an effective amount of the recombinant adenoviral vector or a vaccine composition thereof as disclosed herein. Also provided is use of the recombinant adenoviral vector or the vaccine composition as described herein for manufacturing a medicament (e.g. a vaccine) for inducing an immune response in a subject against enterovirus infection.

The term "an effective amount" refers to a dose or amount sufficient to provide a desired therapeutic effect in a treated subject, for example, sufficient to generate or induce an immune response against a pathogen (e.g. enterovirus) or an antigen (e.g., 3C or 3CD protein of an enterovirus) in the recipient thereof. The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the recombinant adenoviral vector of the invention is administered in a dose of $1\times10^7$ to $1\times10^{12}$ plaque-forming unit (pfu), e.g. $1\times10^7$, $1\times10^8$, $1\times10^9$, $1\times10^{10}$, $1\times10^{11}$, or $1\times10^{12}$ pfu.

The term "immune response" may include, but is not limited to, a humoral response and a cell mediated immune response e.g. $CD^{4+}$ or $CD^{8+}$ cell activation.

A viral vector can be administered via any physiologically acceptable route, such as orally, parenterally (e.g. intramuscularly, intravenously, subcutaneously, and intraperitoneally), nasally, rectally, transdermally or inhalationally. In some embodiments, the viral vector can be administered orally, subcutaneously or intraperitoneally. Immunization can be performed by repeated administration, typically including an initial administration followed by subsequent booster administrations.

It is found in the invention that a 3C specific cellular immunity is sufficient to protect various enterovirus infections. Accordingly, the method of the invention is effective to provide cross-protective immunity against different enterovirus species due to highly conservation of the amino acid sequences of the 3C protein among different species of enterovirus. In certain embodiments, the method of the invention is effective in inducing an immune response against *Enterovirus A*, covering both EV71 and CVA, which are the major causes of HFMD.

The present invention also provides a method for producing virus like particles of an enterovirus in a mammalian cell system, comprising:
  culturing mammalian cells transfected with a recombinant adenoviral vector comprising an expression cassette encoding a P1 protein and a 3CD protease of the enterovirus under conditions that allow the expression of the P1 protein and the 3CD protein and assembly of the virus like particles of the enterovirus; and
  collecting the cultured mammalian cells and isolating the virus like particles of the enterovirus as produced from the cultured mammalian cells.

Transfection can be performed by any known method and can result in either transient or stable transfection. Stable transfection can be conducted to establish a cell line producing VLPs of interest.

In some embodiments, the recombinant adenoviral vector for transfecting mammalian cells is replication competent or deficient.

In some embodiments, the mammalian cells to be transfected by the recombinant adenoviral vector are complementing cells that can complement for a deficiency of the adenoviral genome of the replication deficient adenoviral vector as used. Typical examples of the complementing cells are 293 cells or other cells described in for example U.S. Pat. Nos. 6,677,156, 6,913,927 or US 20030017595.

The VLPs as produced in the mammalian cell system can be collected and formulated with a suitable carrier to form a vaccine composition against enterovirus infections. The VLPs thus prepared according to the present invention can be valuable as a vaccine due to glycosylation status similar to that in human.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

In this study, we have designed and genetically engineered a recombinant adenovirus vector, Ad-EVVLP with the EV71 P1 and 3CD genes inserted into the E1/E3-deleted adenoviral genome. Ad-EVVLP were produced in HEK-293A cells. In addition to Ad-EVVLP particles, virus-like particles (VLPs) formed from the physical association of EV71 capsid proteins, VP0, VP1, and VP3 expressed from P1 gene products. They were digested by 3CD protease and confirmed to be produced by Ad-EVVLP-producing cells, as determined using transmission electron microscopy and western blotting. Mouse immunogenicity studies showed that Ad-EVVLP-immunized antisera neutralized the EV71 B4 and C2 genotypes. Activation of VLP-specific CD4$^+$ and CD8$^+$/IFN-γ T cells associated with Th1/Th2-balanced IFN-γ, IL-17, IL-4, and IL-13 was induced; in contrast, FI-EV71 induced only Th2-mediated neutralizing antibody against EV71 and low VLP-specific CD4$^+$ and CD8$^+$ T cell responses. The antiviral immunity against EV71 was clearly demonstrated in mice vaccinated with Ad-EVVLP in a hSCARB2 transgenic (hSCARB2-Tg) mouse challenge model. Ad-EVVLP-vaccinated mice were 100% protected and demonstrated reduced viral load in both the CNS and muscle tissues. Ad-EVVLP successfully induced anti-CVA16 immunities. Although antisera had no neutralizing activity against CVA16, the 3C-specific CD4$^+$ and CD8$^+$/IFN-γ T cells were identified, which could mediate protection against CVA16 challenge. FI-EV71 did not induce 3C-mediated immunity and had no efficacy against the CVA16 challenge. These results demonstrate that Ad-EVVLP can enhance neutralizing antibody and protective cellular immune responses to prevent EV71 infection and cellular immune responses against CV infection. Ad-EVVLP meets a medical need as a universal HFMD vaccine against both EV71 and CV infections.

1. Materials and Methods 1.1 Ethics Statement

All animal experiments were conducted in accordance with the guidelines of the Laboratory Animal Center of the National Health Research Institutes (NHRI), Taiwan Animal use protocols were reviewed and approved by the NHRI Institutional Animal Care and Use Committee (Approval Protocol No. NHRI-IACUC-100125-A). In EV71 challenge experiments, survival rate was used as an endpoint to assess the protective efficacy of the anti-EV71 treatment. Survival rate used as an index of pathogenesis of EV71 infection has been reported by numerous studies in experimental animal models [16, 19, 21, 22]. After investigation, tested animals were euthanized by 100% CO$_2$ inhalation for 5 min followed by cervical dislocation to minimize suffering. To perform virus challenge, mice were placed in an anesthetic inhalator chamber containing isoflurane (initial phase: 5%; maintenance phase: 1.5%-2.5%) for 1 min before s.c. or i.p. EV71 immunization.

1.2 Cells, Viruses, Compounds, and Antibodies

African green monkey kidney (Vero) (ATCC No. CCL-81) and human rhabdomyosarcoma (RD) (ATCC No. CCL-136) cells were provided by the Taiwan Centers of Disease Control (Taiwan CDC); the original cell lines were obtained from the American Type Culture Collection (ATCC), United States. Vero cells were cultured in a VP-SFM medium (Gibco-Invitrogen, CA, USA) supplemented with 4 mM L-glutamine (Gibco-Invitrogen, CA, USA). The RD cell line was cultured in DMEM medium containing 10% fetal bovine serum (Gibco-Invitrogen, CA, USA). Cells were maintained in a 37° C. incubator equilibrated with 5% CO$_2$. Clinically isolated strains of EV71, E59 (B4) (GenBank: GQ150746.1), Neu (pinf7-54A) strain (C2) (GeneBank DQ060149), Tainan/5746/98 (C2) (GenBank: AF304457.1), and one strain of CVA16, 5079 (GenBank: AF177911.1) were obtained from Dr. Jen-Ren Wang, National Cheng-Kung University, Tainan, Taiwan, and were propagated in Vero cells based on the microcarrier cell culture bioprocess [23,24]. Human adenivirus 5 (Ad5; ATCC No. VR-1516™) was purchased from ATCC and propagated in 293A cells. Virus stocks were stored at −80° C. Virus stock titers were tested in a standard plaque-forming assay [25], and the number of plaque-forming units (pfu) was calculated.

Monoclonal antibody, Mab979 recognized VP0/VP2 capsid protein of EV71 [26] was purchased from Millipore, Inc., MA, USA. A VP1-specific monoclonal antibody E1 produced in house had been described [26]. Antibodies specific to human β-actin (Cat. No. A5441) was purchased from Sigma-Aldrich MO, USA. Horse radish peroxidase (HRP)-conjugated donkey anti-mouse antibody (Cat. No. 715-036-150) or HRP-conjugated rabbit anti-goat antibody (Cat. No. 305-035-003) were purchased from Jackson Immunoresearch, Inc., PA, USA.

1.3. Construction and Production of Ad-EVVLPI and Ad-EVVLPI

The P1 and 3CD genes of the EV71 Neu (pinf7-54A) strain were amplified by PCR and individually inserted into the shuttle vector pENTR4 (Invitrogen). The nucleotide element of the elongation factor-1α (EF-1α) promoter was inserted into the 3' end of the P1 gene and the 5' end of the 3CD insert to generate the pENTR4-P1/EF-1α/3CD construct. The 3CD gene alone was inserted into pENTR4 to generate the pENTR4-3CD construct. The pENTR4-P1/EF-1α/3CD and pENTR4-3CD constructs were enzymatically recombined into the ΔE1/ΔE3 (replication-incompetent) Ad5 vector pAd/CMV/V5-DEST [27] to form recombinant pAd-EVVLP and pAd-3CD, respectively. pAd DNA was transfected into the 293A packaging cell line to produce the recombinant adenoviruses designated Ad-EVVLP and Ad-3CD. Ad-LacZ carrying a luciferase reporter gene as a vector control was obtained from Invitrogen. The recombinant viruses were purified and concentrated using Vivapure adenoPACK 100RT (Satorius Stedin Biotech). The purified virus titers were determined using a modified standard plaque assay. Various Ad virus dilutions were added to each well of 293A cells plated in a 6-well tissue culture plate. After overlaying the cultures with DMEM containing 0.75% methylcellulose, the cultures were incubated at 37° C. for 10 to 12 days and plaques were counted. The typical yield of adenoviruses was approximately 1×10$^9$ pfu/mL.

1.4. Western Blot

Western blotting was performed as described previously [25]. Total cell lysates were prepared by treating 1 to 2×10$^6$ cells with 100 μL ice cold lysis buffer (0.5% sodium deoxycholate, 0.1% sodium dodecyl sulfate (SDS), 0.5% NP-40, 50 mM TRIS, 150 mM NaCl) plus a protease inhibitor cocktail (Roche, French) and 1 mM PMSF (Sigma-Aldrich, CA, USA). Lysates were centrifuged for 20 min at 10,000 rpm at 4° C. to sediment the cell debris. The protein concentration of the cell lysates or fractions was measured using the Bradford method [28]. Cell lysates containing 10 μg protein were mixed with loading dye and loaded into each well of a 10% SDS-polyacrylamide gel (SDS-PAGE, Amersham Biosciences-GE Healthcare, USA) and subjected to electrophoresis in 1× Tris-glycine SDS-running buffer. The resolved proteins were transferred onto nitrocellulose membrane (Hybond-ECL, Amersham Biosciences-GE Healthcare, USA). Membranes were soaked in 5% skim milk in 1×PBS for 30 min at room temperature, then washed 3 times with 1×PBS plus 0.05% Tween 20 (PBS-T). The membrane was incubated with rat anti-3C (1:1000), MAB979 (1:5000), or anti-VP1 antibody (1:1000) for 14 to 16 h at 4° C. and subsequently washed with PBS-T followed by incubation with HRP conjugated anti-rat or donkey anti-mouse (for MAB979) antibodies. After 1 h incubation, the membrane was washed 5 times with PBS-T, and then Super Signal West Pico chemiluminescent substrate (Pierce, Ill., USA) was layered onto the membrane, and it was exposed to X-ray film (Kodak, N.Y., USA). When necessary, the membranes were stripped using Restore buffer (Pierce, Ill., USA) and blotted with another antibody.

1.5 Flow Cytometry

Splenocytes were harvested from BALB/c mice and labeled with 5-(6)-carboxyfluorescein diacetate succinimidyl ester (CFSE) (Cat. No. C34554, Molecular Probes). They were restimulated in vitro with $10^7$ pfu/mL UV-inactivated EV71 5746 or 1.4 µg/mL purified recombinant E59 3C proteins expressed by E. Coli. (provided by Dr. Pete Chong, a coauthor of this study) for 5 days. Proliferation of splenocytic CD4$^+$ T cells was analyzed by flow cytometry (BD FACSCalibur) using PE-Cy5-labeled anti-CD4 antibodies. The population of no fluorescence signal-shifting in CFSE-prestained CD4$^+$ T cells without antigen stimulation was set to 0%, and the population of negatively shifted CD4$^+$ T cells (proliferating cells) after antigen stimulation was quantified. The mean percentage corresponding to the individually proliferating CD4$^+$ T cells in each group was calculated. To detect the population of CD8$^+$IFN-γ$^+$ T cells, splenocytes were cocultured with the EV71 antigen for 2 days and then with brefeldin A (Cat. No. 00-4506-51, eBioscience) for 3 h before harvesting. Stimulated splenocytes were stained with PE-Cy5-labeled anti-CD8 antibody for 30 min, followed by subsequent fixation and permeabilization. A portion of these cells was further stained with PE-conjugated anti-IFN-γ$^+$ antibody (BD Bioscience) for 30 min to detect intracellular IFN-γ. After washing, the samples were analyzed by flow cytometry.

1.6 PCR and Real Time RT-PCR pAd-EVVLP plasmid DNA was used as a template to detect the P1, 3CD, and EF-1α promoter regions within pAd-EVVLP by PCR using the respective primer pairs. The PCR conditions were as follows: 95° C. for 3 min; 35 cycles at 95° C. for 1 min, 60° C. for 1 min, and 72° C. for 3 min; and a final incubation at 72° C. for 2 min.

Total RNA was purified from tissues using TRIZOL reagent (Invitrogen, CA, USA) following the manufacturer's instructions and was subjected to real time RT-PCR. Total RNA was converted into cDNA using random primers (Genomics BioSci&Tech, Taiwan) and reverse transcriptase (Bionovas, Toronto, Canada). The synthesized cDNA was subjected to quantitative PCR analysis (LightCycler 480 SYBR Green Real-Time PCR system) using primer pairs specific to the VP1 region of EV71 P1 RNA. Human β-actin gene expression was used as an internal control. The PCR conditions were as follows: 95° C. for 3 min; 40 cycles at 95° C. for 10 s, 65° C. for 20 s, and 72° C. for 2 s; and a final incubation at 72° C. for 2 min. The number of cycles required for amplification of transcripts was obtained. The relative expression of EV71 P1 RNA was calculated as follows: the individual Ct obtained from the experimental group or control group was subtracted by its respective Ct (β-actin) to gain normalized Ct, and then $2^{Normalized\ Ct\ (VP1\ of\ P1\ RNA\ from\ the\ sample\ without\ viral\ infection)}$ was divided by $2^{Normalized\ Ct\ (VP1\ of\ P1\ RNA\ from\ the\ sample\ with\ viral\ infection)}$. The forward and reverse primers, [5_-ACGCGCAAATGCGTA-GAAAGGT-3_-forward (SEQ ID NO: 7) and 5_-TTAGTG-GCAGTTTGCCATGCGA-3_-reverse (SEQ ID NO: 8)], were used to amplify and detect VP1 RNA. human β-actin mRNA was amplified using the primer pairs 5_-AC-CAACTGGGACGACATGGAGAAA-3_-forward (SEQ ID NO: 9) and 5_-TAGCACAGCCTGGATAGCAACGTA-3_-reverse (SEQ ID NO: 10). Primer pairs targeting the P1, 3CD, and EF-1α promoter regions of Ad-EVVLP are as follows: P1: 5_-ATCG GAATTCATGGGCTCACAGGT-GTCCAC-3_-forward (SEQ ID NO: 11) and 5_-CTTGTC-GACTTAGAGAG TGGTAATTGCTG-3_ (SEQ ID NO: 12)-reverse, 3CD: 5_-ATCGGAATTCATGGGGC-CGAGCTTGGAC-3_-forward (SEQ ID NO: 13) and 5_-ATCGCTCGAGAAACAATTCGAGCC-3_-reverse (SEQ ID NO: 14), EF-1Δ promoter: 5_-ATCGACGCGT-GTGAGGCTCCGGTGCCC-3_-forward (SEQ ID NO: 15) and 5_-ATCGCCCGGGGTTTTCACGACACCTG-3_-reverse (SEQ ID NO: 16). All primer sets were commercially synthesized by Genomics BioSci&Tech, Taiwan.

1.7 Density Gradient Purification of EV71 VLP and Ad

HEK-293A cells ($1\times10^7$) were seeded in a 10-well plate 1 day prior to Ad-EVVLP infection with MOI=1. After 24 h of infection, the cells were harvested and lysed in 1% NP-40 lysis buffer (50 mM Tris/HCl, pH 7.5, 150 mM NaCl, 2 mM EDTA, and 1% NP-40) on ice for 30 min and centrifuged at 1000×g for 10 min to remove the cell debris. The supernatants were harvested and concentrated by ultracentrifugation at 100,000×g for 1 h at 4° C. and then dissolved in 30 µL PBS. The samples were loaded into self-generated iodixanol gradients, which were prepared by mixing 0.6 mL solution S (0.25 M sucrose, 15 mL EDTA, 30 mM Tris/HCl, pH 8.0) and 0.42 mL 60% (w/v) iodixanol (Cat. No. 1114542, Optiprep; Axis Shield, UK) to form a homogenous solution. Gradients were generated through centrifugation at 162,000×g for 24 h at 4° C. The various fractions were manually harvested from the top (named Fraction No. 1), 0.1 mL per fraction, and 10 fractions were serially collected for each sample. These fractions were subjected to Western blot using Mab979 antibodies or transmission electron microscopy.

1.8 Transmission Electron Microscopy

HEK-293A cells were harvested 24 h after Ad-EVVLP infection, and cell pellets were frozen and thawed twice at −80° C. for 30 min and 37° C. for 15 min. Lysates were centrifuged at 3000 rpm for 15 min at room temperature, and supernatants were harvested and subjected to examine adenovirus using a JEOL JEM-1400 transmission electron microscope (TEM). The lysate was fractionated through density gradient centrifugation, and fractions were concentrated through ultracentrifugation at 100,000×g for 1 h and resuspended in 200 µL PBS. The fractions were then cleaned by centrifugation in a 100 KDa-cut-off spin-X$^R$ UF 20 column (Corning). Samples were treated with uranyl acetate and inspected by TEM.

1.9 ELISA

To detect anti-EV71, anti-Ad, or anti-3C antibodies in sera, 96-well plates were coated with 100 µL per well of heat-inactivated (56° C. for 1 h) $10^3$ pfu EV71 5746 (C2 genotype) or E59 (B4 genotype) strains, 200 pfu purified Ad5, or 700 ng recombinant 3C protein in carbonate coating buffer. Serum samples collected from immunized mice were inactivated at 56° C. for 30 min. Two-fold serial dilutions of the sera were performed beginning from an 8-fold initial dilution. The diluted sera were added to the wells and incubated at room temperature for 2 h. After washing with PBS-T, HRP-conjugated donkey anti-mouse IgG antibodies were added to the wells for 45 min. The reaction was developed by incubation with 100 µL TMB substrate (3, 3',5,5'-etramethyllbenzidine) for 20 min in the dark and terminated by adding 50 µL 2 N H$_2$SO$_4$. The optical density at 450 nm was determined using a microplate absorbance reader (SPECTRA, MAX2, M2). To detect cytokines secreted by splenocytes, the supernatants from 2-day cultures of splenocytes restimulated with $10^7$ pfu/mL UV-inactivated EV71 5746 were analyzed using a calorimetric sandwich IFN-γ, IL-4, IL-13, and IL17A ELISA kit (Cat. No. 887314, 88-7044, 88-7137, and 88-7371, respectively, eBioscience). The assays were conducted according to the manufacturer's instructions, and the optical densities at 450 nm were determined using a microplate absorbance reader.

1.10 Neutralizing Assay

To detect the neutralizing activity as described in our previous study [26], each sample was serially diluted 2-fold in fresh cell culture medium. A total of 100 μL 100 $TCID_{50}$ virus suspension, E59, 5746, or CVA16 strain was added to each tube containing 100 μL serially diluted serum. After incubation at 4° C. for 18 to 24 h, 100 μL virus serum mixture was added to 96-well plates seeded with rhadomyosarcoma (RD) cells and incubated for 7 days at 37° C.; $TCID_{50}$ values were measured by counting cytopathic effects (CPE). The 50% neutralization inhibition dose (ID50) was calculated as the reciprocal of the serum dilution compared to normal serum using the Reed-Muench method [29]. A mouse anti-EV71 Mab979 antibody (Chemicon International) was used as an internal positive control.

1.11 Enzyme-linked Immunosorbent Spot Assay

Suspensions containing $5 \times 10^6$ RBC-free splenocytes were prepared from individual mice and seeded in individual wells of 96-well filtration plates (Millipore) pre-coated with capturing monoclonal antibodies for murine IL-4 or IFN-γ (0.5 μg/well) (Cat. No. 16-7041-68 or 16-7313-68, respectively, eBioscience) and blocked with conditioned medium (CM) for 1 h at room temperature. The splenocytes were added to $10^6$ pfu/well UV-inactivated EV71 5746 dissolved in CM (100 μL). Splenocytes incubated with Con A (10 μg/mL) were used as a positive control. Unstimulated splenocytes were used as a negative control. Plates were maintained in a 37° C. incubator equilibrated with 5% $CO_2$ for 48 h. The individual wells of the ELISPOT plates were washed 3 times with PBS-T, and 0.2 μg of the corresponding biotinylated detection monoclonal IL-4- or IFN-γ-specific antibody was added to detect the respective cytokines. The plates were washed after 2 h incubation at room temperature, and 100 μL streptavidin-alkaline phosphatase (1:250 dilution) was added to the individual wells. The plates were incubated at room temperature for 45 min Finally, the plates were washed 4 times with wash buffer, and 100 μL AEC (3-amine-9-ethylcarbazole, Sigma-Aldrich) substrate was added to each well and allowed to react for 30 min at room temperature in the dark. The plates were washed with water, air-dried overnight, and the spots on each well were scored using an immunospot counting reader (Immunospot, Cellular Technology Ltd.). The results were expressed as the number of cytokine-secreting cells per $5 \times 10^5$ splenocytes seeded in the initial culture.

Figure 2:
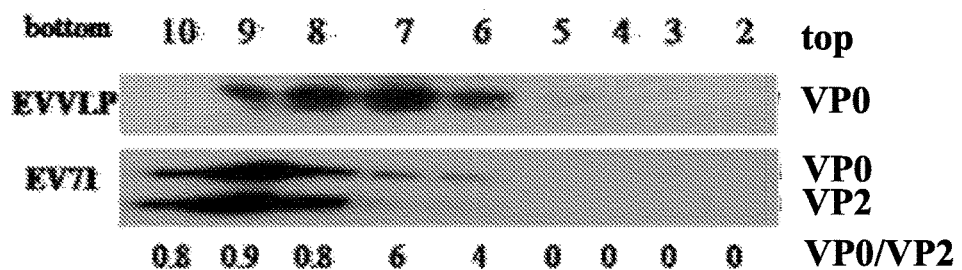
Figure 2:
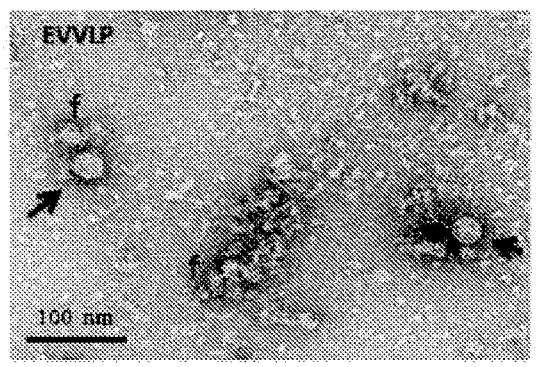
Figure 2:
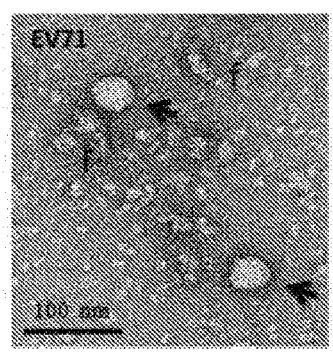
Figure 2:
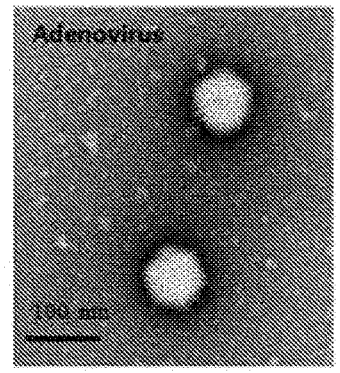
Figure 2:
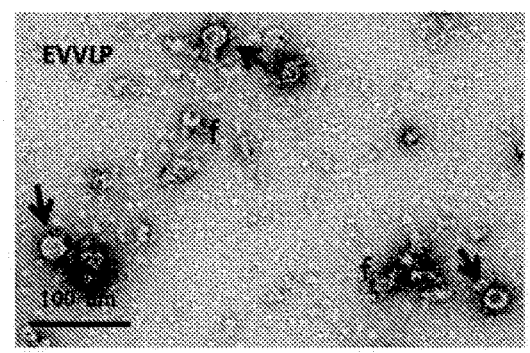

1.12 Ad-EVVLP Vaccination of hSCARB2 Transgenic Mice Challenged with EV71 and CVA16 hSCARB2-Tg mice in a C57BL/6 background generated were previously generated by our group and were maintained by cross-mating hSCARB2-Tg subjects to obtain inbred mice [16]. One-day-old hSCARB2-Tg mice were inoculated s.c. with PBS, $3\times10^7$ pfu Ad-LacZ, or $3\times10^6$ or $3\times10^7$ pfu Ad-EVVLP, or 1 μg FI-EV71 vaccine on Days 1 and 7, and then challenged s.c. with $3\times10^6$ pfu EV71 5746 or $5\times10^5$ pfu CVA16 on Day 14. The mice were monitored daily for survival for 15 days after the challenge.

1.13 Statistical Analysis

Logrank test was used to analyze the difference in survival rate of drug-treated and non-treated transgenic mice. The unpaired t test with Welch's correction statistic was used to analyze the difference of the tested gene expression between experimental groups. Results are considered statistically significant with a p value of $<0.05$. The symbols * and ** are used to indicate p values $<0.05$ and $<0.01$, respectively.

2. Results 2.1 Ad-EVVLP and VLP Production in HEK-293A Cells

We used the E1- and E3-deleted adenovirus-5 genome to construct the Ad-EVVLP expression vector, which carried full-length P1 and 3CD genes of EV71 (FIG. 1A). We performed polymerase chain reaction (PCR) to confirm the inserts: P1, 3CD, and elongation factor-1α promoters (EF-1p) using the respective primers in the Ad-EVVLP construct. The PCR products corresponded to 2585 bps (P1), 2020 bps (3CD), and 1186 bps (EF-1p) (FIG. 1B). Upon transfection in competent HEK-293A cells constitutively expressing the E1 protein, the recombinant Ad was generated. We examined Ad-EVVLP and the control Ad-LacZ by western blot using the polyclonal anti-Ad5 antibody. They each expressed Ad structural proteins, including hexon, penton, and protein V, VI, and VII (FIG. 1C). Previous studies have shown that multiple capsid proteins of VP0 (38 KDa, a precursor product of VP2+VP4), VP1 (36 KDa), VP2 (28 KDa), VP3 (25 KDa), and VP4 (8 KDa) can be detected in EV71-infected cells [26,30]. The VLP expression by Ad-EVVLP was characterized; translated products of EV71 VLPs, including VP0 (a precursor of VP4-VP2) but not VP2, were detected in 293A cells using the VP2-specific monoclonal antibody Mab979 [47]. EV71 antigens VP0 and VP2 were detected by Western blotting (FIG. 1C). We confirmed VP1 expression using a VP1-specific antibody, which corresponded to the 34 to 36 kDa bands in Ad-EVVLP-infected lysates and in the sample of EV71 antigens (FIG. 1C). The antigenic profile of VLPs expressed by Ad-EVVLP was similar to E-particles (composed by VP0, VP1, and VP3) from EV71, which does not contain viral RNA, compared to F-particles (composed by VP2, VP4, VP1, and VP3) [30]. In addition, 3C' processed the P1 polyprotein to form VP0, VP1, and VP3 in the absence of EV71 genetic RNA [30]. We detected an 18 kDa band using an anti-3C antibody. In contrast, we could not detect these bands in uninfected or Ad-LacZ-transfected 293A cells (FIG. 1C). However, no VP3-specific antibody is available to detect VP3. We could not detect a VP3 signal by blotting with sera from EV71-infected mouse (FIG. 9).

To demonstrate that the EV71 VLP particles were cogenerated in Ad-producing cells, we purified the virions from the cytosol of Ad-EVVLP transfectant using fractionation through density gradient centrifugation. We fractionated EV71 particles as a control. We characterized each fractionated sample by Western blot analysis using Mab979. The major band was 38 kDa, corresponding to VP0, but there was minor expression of a 28 kDa corresponding to VP2 (intensity ratio of VP0/VP2=4 and 6, respectively), which together make the E-particle of EV71 in Fractions 6 and 7. In contrast, the opposite pattern of VP0/VP2 expression (0.8, 0.9, and 0.8, respectively) corresponding to F-particles was observed in Fractions 8, 9, and 10. However, only VP0 signals were detected in Fractions 6 to 9 of Ad-EVVLP-infected lysate (FIG. 2A). A similar antigenic profile of EV71 has been previously reported [31].

We pooled Fractions 7 and 8 of Ad-EVVLP samples and examined them by TEM. TEM analysis revealed some fractured VLPs (f) and cellular impurities in the samples due to sample preparation. Two sizes of complete particles were also present; particles over 100 nm in diameter corresponded to Ad particles (FIG. 2D), and particles approximately 30 nm in diameter corresponded to VLPs expressed by Ad-EVVLP (FIG. 2B). EV71 particles in the pool of Fractions 8 and 9 of EV71 samples were also examined (FIG. 2C).

2.2 EV71 VLP-specific Humoral Responses in Ad-EVVLP-immunized Mice

To examine the immunogenicity of Ad-EVVLP compared to the FI-EV71 vaccine, we intraperitoneally (i.p.), subcutaneously (s.c.), or orally administered adult BALB/c mice with $1 \times 10^8$ pfu of Ad-EVVLP or Ad-LacZ on Days 1 and 14. Animals in separate groups were s.c. administered 0.1 μg or 1 μg FI-EV71 twice to evaluate the virus-specific immune responses compared with those of recombinant adenoviruses. The results of ELISA assays showed (FIG. 3A) that the mean anti-EV71 titer against EV71 5746 (C2 subgenotype) in Ad-EVVLP-immunized serum samples collected on Day-21 were 2240, 7040, and 130 for s.c., i.p., and orally, respectively. We did not detect a titer in serum from s.c. Ad-LacZ-immunized mice (FIG. 3A). The mean titer of serum antibodies reacting with the EV71 E59 strain (B4 subgenotype) from the Ad-EVVLP-immunized animals was to 2240, 8960, and 180, for s.c., i.p., or orally, respectively. Again, no E59 reactivity was detected in serum of the mice immunized with Ad-LacZ (FIG. 3B). Sera from Ad-EVVLP-immunized mice possessed EV71 neutralizing activity (Table 1). Higher virus neutralization titers (1/128) were found in i.p. and s.c. Ad-EVVLP-immunized mice compared to a considerably low neutralizing titer in orally administered animals. Neutralizing antibodies produced in Ad-EVVLP-immunized mice exhibited potent neutralizing activity against EV71 B and C strains. Comparable titers (1/256 and 1/512) of neutralizing antibody in the mice s.c. administered 0.1 μg FI-EV71 vaccine. No anti-CVA16 neutralizing activity was found in the serum from mice immunized with Ad-EVVLP, FI-EV71 vaccine, or PBS (<1:8; Table 1). These results are consistent with previous reports [32] that FI-EV71 vaccine could not elicit cross-neutralizing antibody against CVA16.

TABLE 1

Induction of neutralizing antibodies against EV71 E59 and 5746 strains and CVA16 by Ad-EVVLP or FI-EV71 vaccine.

| | Route | Strain | EV71-specific neutralizing antibody titers (mean) |
|---|---|---|---|
| Ad-LacZ | i.p/s.c/oral | E59/5746/CVA16 | <1:8 |
| Ad-EVVLP | i.p. | E59 | 1:64 |
| | | 5746 | 1:128 |
| | | CVA16 | <1:8 |
| | s.c. | E59 | 1:64 |
| | | 5746 | 1:64 |
| | | CVA16 | <1:8 |
| | oral | E59 | <1:8 |
| | | 5746 | <1:8 |
| FI-EV71 (0.1 μg) | s.c. | E59 | 1:256 |
| FI-EV71 (1 μg) | s.c. | 5746 | 1:512 |
| | | CVA16 | <1:8 |

*Seven-week-old BALB/c mice were individually primed and boosted at 14-day intervals i.p., s.c., or orally with $10^8$ pfu Ad-EVVLP or Ad-LacZ. Sera collected on Day 21 were analyzed for neutralizing activity by incubating $10^2$ pfu 5746, E59 or CVA16 with varying dilutions of individual immune sera before being added to RD cells. CPE was observed after 5 days of culture. The results are expressed as neutralizing titers that correspond to the dilution of immune sera, giving $TCID_{50}$ value of 50% reduction of cytopathic effect.

2.3 Induction of VLP-specific Cellular Immunities in Ad-EVVLP-immunized Mice

Figure 10:
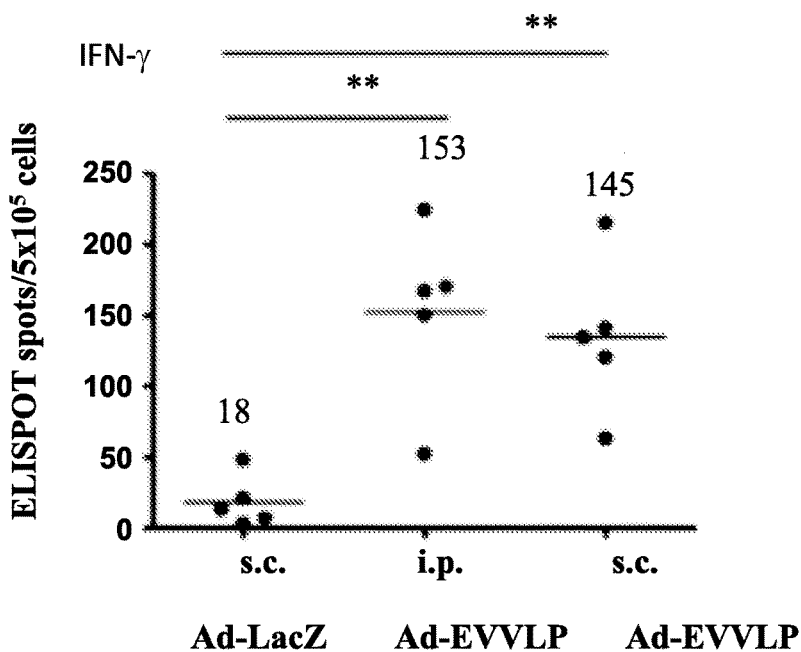
FIG. 10 shows enumeration of IFN-γ and IL-4-secreting cells in spleens of Ad-EVVLP-immunized mice. Splenocytes prepared from mice immunized twice with Ad-LacZ or Ad-EVVLP i.p. or s.c. were cultured and supplemented with murine IL-2 in the presence of UV-EV71 E59 in anti-IFN-γ (A) or anti-IL-4 (B) capture antibody-coated wells of an ELISPOT plate for 2 days. Cytokine-positive immunospots were developed using the reagents and protocol provided in the assay kit. The results are expressed as the number of specific cytokine immunospots ±2 standard deviations for each group.
Figure 10:
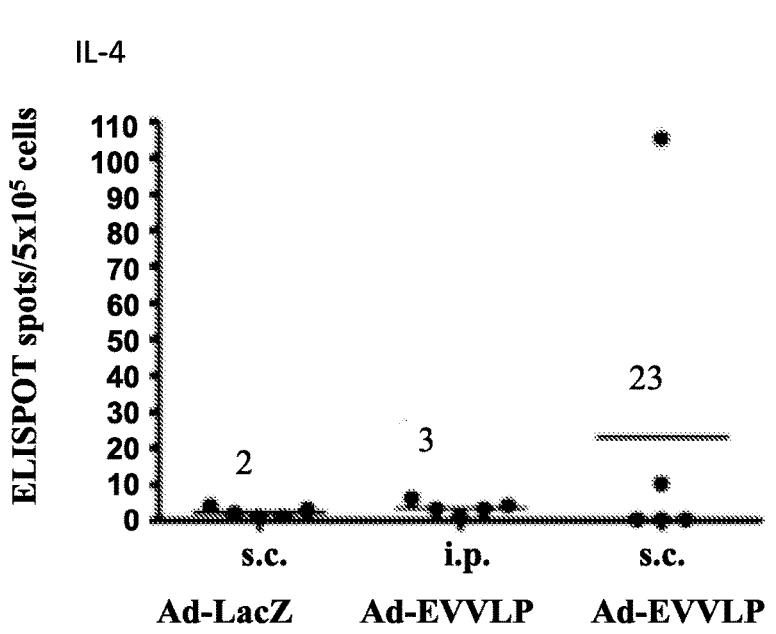

Recent studies on host immune responses against EV71 have suggested that T cell immunity plays a critical role in the protection against EV71 infection and control of the disease [33,34]. Therefore, we investigated whether the VLP-specific CD4$^+$ and CD8$^+$ T cell responses could be elicited in Ad-EVVLP-immunized mice. Seven days post-immunization, we isolated lymphocytes from the spleen, followed by in vitro restimulation with UV-inactivated EV71 (UV-EV71). Lymphocytes from Ad-LacZ-immunized mice produced background IFN-γ levels. In contrast, substantially higher IFN-γ levels were measured in lymphocyte cultures from mice administered Ad-EVVLP (FIG. 4A). Lymphocytes from FI-EV71 vaccine-immunized mice secreted background IFN-γ levels (FIG. 4A). Within the panel of Th2 cytokines assayed, IL-4 (FIG. 4B) and IL-13 (FIG. 4C) were moderately secreted by lymphocytes from Ad-EVVLP-immunized mice, indicating that balanced Th1/Th2 responses were activated. Interestingly, immunization of the FI-EV71 vaccine led to the production of the highest IL-4 and IL-13 levels, indicating that a Th2 biased response was induced (FIGS. 4B and 4C). This result supports our findings that FI-EV71 vaccination in hSCARB2-Tg mice induced splenocytic IL-4 but not IFN-γ secretion, as shown previously [16]. The results obtained from IFN-γ and IL-4 ELISPOT assays confirmed that i.p. Ad-EVVLP immunization induced significant splenocytic IFN-γ production and low levels of IL-4 secretion in Ad-EVVLP-vaccinated mice (FIG. 10). A considerable amount of IL-17A was produced by splenocytes from Ad-EVVLP-immunized mice in response to EV71 antigens. This was in sharp contrast to the barely detectable amount of IL-17 secreted by splenocytes of animals immunized with Ad-LacZ or the FI-EV71 vaccine (FIG. 4D). These results indicate that Ad-EVVLP drives T cell activation, leading to the differentiation of a subpopulation of T cells that bear the Th1, Th2, and IL-17 producing phenotypes.

Figure 5:
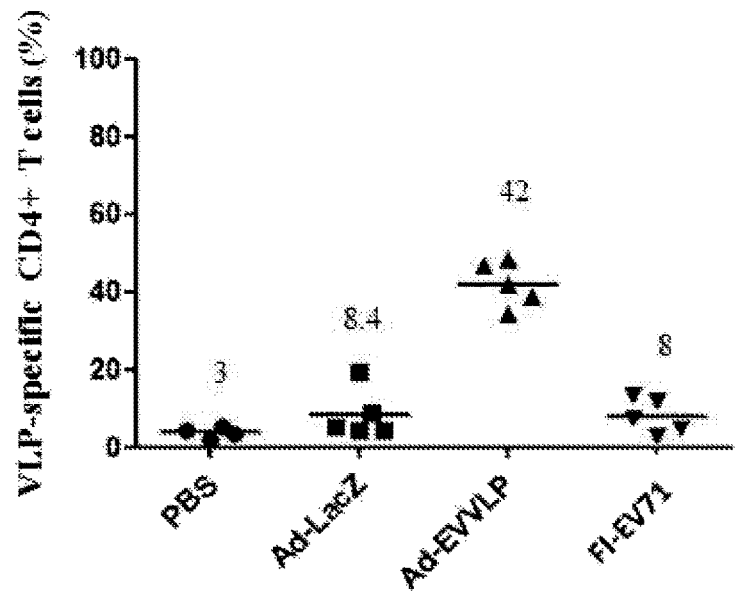
Figure 5:
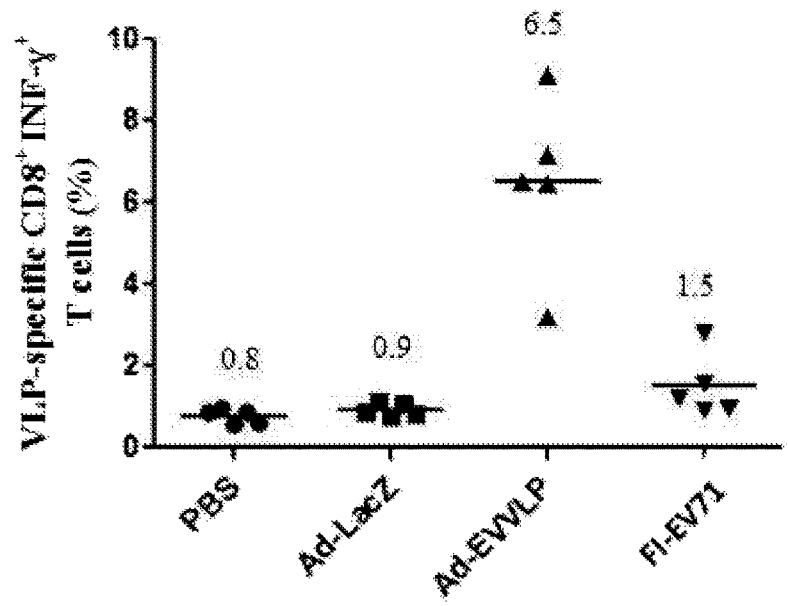

We measured VLP-specific CD4$^+$ T cell proliferation in vaccine-immunized splenocytes followed by restimulation with UV-EV71 by examining the negative shift of fluorescent signal in 5-(6)-carboxyfluorescein diacetate succinimidyl ester (CFSE)-prestained CD4$^+$ T cells using flow cytometry. Compared to little or no shift of signals in the PBS- and Ad-LacZ-immunized groups (3% and 8.4%, respectively), a substantial shift was detected in Ad-EVVLP-immunized group (42%; FIG. 5A). The proliferation of CD4$^+$ T cells corresponding to UV-EV71 was barely detectable in the FI-EV71-immunized mice (8%; FIG. 5A), indicating that the antigenicity of FI-EV71 reacting to VLP was altered, and therefore the immunized CD4$^+$ T cells could not be fully reactivated by exposure to EV71 particles. We further examined the response of VLP-specific CD8$^+$ T cell activation in Ad- and FI-EV71-vaccinated animals. After UV-EV71 restimulation, we stained splenocytes with fluorescence dye-conjugated antibodies reacting to surface CD8 molecules and intracellular IFN-γ and analyzed the cells by flow cytometry. We found that the number of CD8$^+$IFN-γ$^+$ T cells in Ad-EVVLP-immunized mice (6.5%) was higher than in Ad-LacZ- or FI-EV71-immunized mice (0.9% or 1.5%, respectively; FIG. 5B). These results suggest that Ad-EVVLP activates EV71 VLP-specific cellular immunity.

Figure 6:
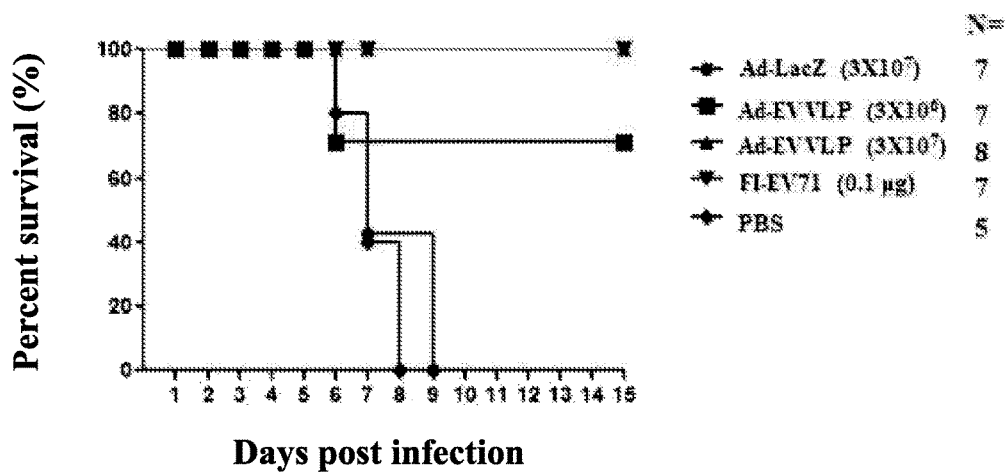
Figure 6:
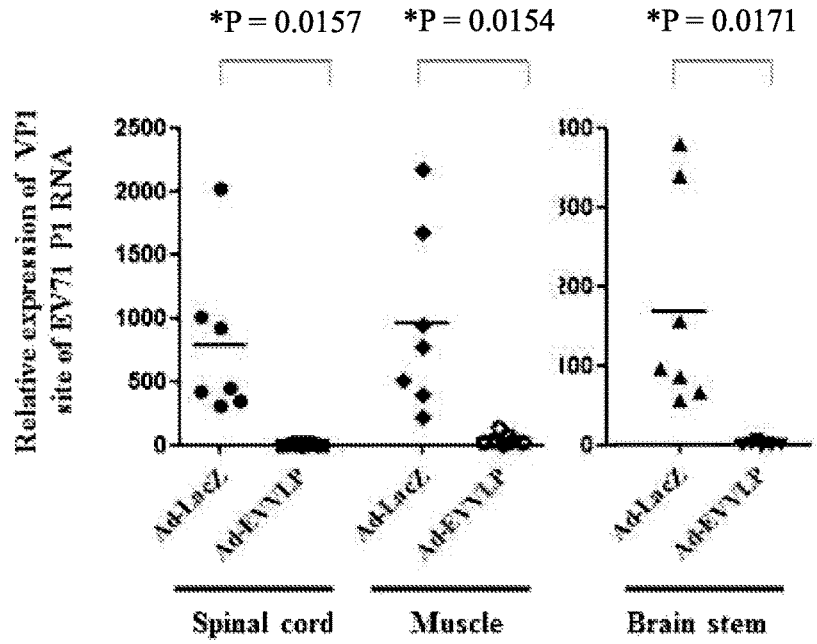

2.4 Ad-EVVLP Vaccine Confers Protection Against EV71 Infection in hSCARB2-Tg Mice We further assessed the efficacy of Ad-EVVLP in protecting against EV71 infection using the hSCARB2-Tg mice model. One-day-old hSCARB2-Tg mice were primed and s.c. boosted with Ad or FI-EV71 vaccine on Days 1 and 7, followed by s.c. challenge of $3 \times 10^6$ pfu EV71 5746 strain 14 days after birth. Mice were monitored daily for survival. As shown in FIG. 6A, mice immunized with $3 \times 10^7$ pfu Ad-LacZ or PBS died 8 to 9 days after challenge. In contrast, 75% of the mice survived after receiving as little as $3 \times 10^6$ pfu of Ad-EVVLP, and 100% of the mice survived when injected with a 10-fold higher dose of Ad-EVVLP. In comparison, EV71-challenged mice received 0.1 µg FI-EV71 vaccine and 100% of the mice survived (FIG. 6A), indicating that the protective efficacy of Ad-EVVLP against EV71 infection was comparable to the FI-EV71 vaccine. We further examined the viral loads in different tissues of vaccine-immunized animals followed by viral challenge. We extracted RNA from various organs of EV71-challenged Tg mice on Day 4 post-infection to quantify EV71 transcripts using real time RT-PCR with VP1 region-specific primers. Ad-EVVLP immunization substantially reduced VP1 expression in the brainstem, spinal cord, and muscle, compared to considerably high expression in Ad-LacZ-vaccinated mice (FIG. 6B), confirming that Ad-EVVLP can suppress EV71 infection and replication.

2.5 3C-specific Immune Responses Generated in Ad-EVVLP-immunized Mice 3C and 3D are proteins conserved between EV71 and CVs (A16, A6, A10, and A4) that share at least 90% homology in their amino acid sequences (Table 2).

TABLE 2

Comparison of 3CD protein sequence in different strains of enteroviruses

| Strain | | GenBank Accession | % Amino acid identity to in pinf7-54A 3C region | % Amino acid identity to in pinf7-54A 3D region |
|---|---|---|---|---|
| Enterovirus A71 (C2 type) | pinf7-54A | AAY59418 | 100 | 100% |
| Coxsackievirus A16 | CA16/GD09/24 | AGC82916 | 92.896 | 92.208% |
| Coxsackievirus A6 | TW/399/10 | AFO12669 | 94.536 | 91.991% |
| Coxsackievirus A10 | Kowalik | AAR38847 | 91.257 | 94.589% |
| Coxsackievirus A4 | High Point | AAR38842 | 93.989 | 93.074% |

Figure 11:
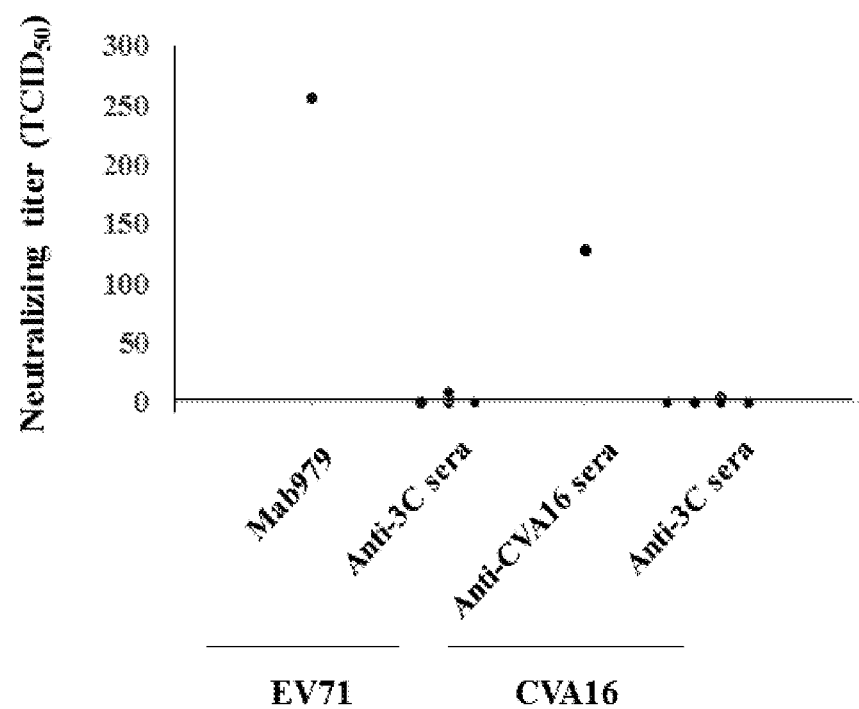
FIG. 11 shows that mouse sera from recombinant 3C adjuvanted with CFA/IFA do not elicit neutralizing activity against EV71 and CVA16. Seven-week-old BALB/c mice were individually primed s.c. with 10 µg recombinant 3C adjuvanted with CFA (3C-CFA) and then s.c. boosted with the same dose of 3C-IFA at 14-day intervals. Sera collected on Day 21 were assayed for neutralizing activity by incubating $10^2$ pfu EV71 or CVA16 with varying dilutions of individual immune sera before being added to RD cells. CPE were observed after 5 days of culture. The results are expressed as neutralizing titers that correspond to the dilution of immune sera, giving $TCID_{50}$ value of 50% reduction of cytopathic effect. Five mice per group were assayed. Varying dilutions of Mab979 antibody and serum collected from BALB/c mice infected with $10^6$ pfu CVA16 at 14 days post-infection for neutralizing EV71 and CVA16, respectively, were included as positive controls.

We examined whether 3C-specific immunities were induced by Ad-EVVLP vaccination. We collected and assayed serum from mice on Day 7 post-prime-boost s.c. with Ad-EVVLP, Ad-LacZ, or FI-EV71. Serum from Ad-EVVLP-immunized mice elicited activity against 3C protein in a recombinant 3C-protein-coated ELISA capturing assay. Anti-3C binding activity was not detected in serum from Ad-LacZ- or FI-EV71-immunized mice (FIG. 7A). Like antisera obtained from FI-EV71, antisera from Ad-EVVLP-immunized mice showed no virus neutralizing activity against CVA16 (Table 1). Moreover, serum from mice primed with 10 µg recombinant 3C protein formulated with complete Freund's adjuvant (CFA) and boosted with the same dose of 3C protein adjuvanted with incomplete FA (IFA) at an interval of 14 days elicited 3C-binding activity, but did not neutralize EV71 or CVA16 infection (FIG. 11). Taken together, these results suggest that the induction of 3C-specific antibody does not contribute to the protection against EV71 infections.

Figure 7:
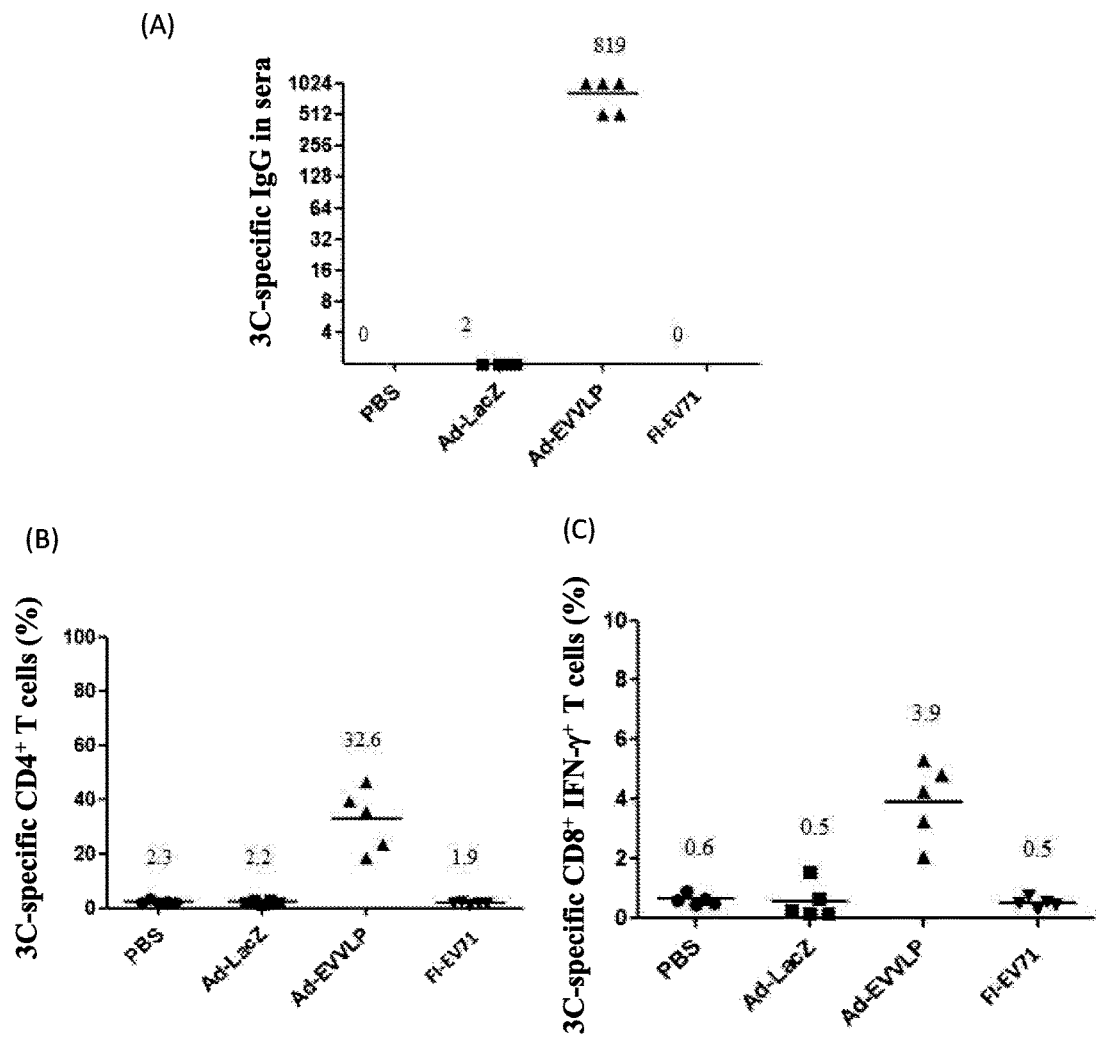
FIG. 7 shows induction of 3C-specific antibody and CD4+ and CD8+ T-cell responses in Ad-EVVLP-immunized mice. BALB/c mice were individually primed and boosted at an interval of 14 days s.c. with PBS, $10^8$ pfu Ad-EVVLP or Ad-LacZ, or 0.1 µg FI-EV71. Mice were sacrificed, and serum and splenocytes were collected on Day 21. (A) Serum was assayed for IgG against recombinant 3C-immobilized ELISA. The results are expressed as titers for each test sample. Bars correspond to the mean titers for each experimental group. Splenocytes were cultured in the presence or absence of 1.4 µg recombinant 3C protein for 48 h. (B) The proliferation of CD4+ T cells in response to 3C was analyzed by flow cytometry with PE-Cy5 antibodies against CD4. (C) Activated CD8+ T cells in splenocytes were stained with PE-Cy5-conjugated anti-CD8 antibodies and subsequently fixed and stained with PE-conjugated anti-IFN-γ antibody, and then analyzed using flow cytometry. The results are presented as the mean percentage of CD4+ or CD8+ T cells after antigen stimulation, compared to gated CD4+ T cells without antigen stimulation that was set at 0%. Five mice per group were assayed.

We further examined 3C-specific cellular immunity in mice immunized with Ad-EVVLP. We isolated splenocytes on Day 7 after vaccine boost and restimulated them with recombinant 3C protein in vitro and observed of $CD4^+$ and $CD8^+$ T cell activation by flow cytometry (FIG. 7). $CD4^+$ T cells from the Ad-EVVLP-immunized group responding to 3C were activated (mean=32.6%), but there were no or minimally activated splenocytes in the PBS-, Ad-LacZ-, and FI-EV71-immunized mice (mean=2.3%, 2.2%, and 1.9%, respectively; FIG. 7B). Activated $CD8^+≥(CD8^+IFN-γ^+)$ T cells corresponding to 3C protein in the Ad-EVVLP-immunized splenocytes were markedly activated (mean=3.8%), in contrast to the minimal $CD8^+IFN-γ^+$ T cells in Ad-LacZ (mean=0.5%) or FI-EV71 (mean=0.5%) and background levels of $CD8^+IFN-γ^+$ T cells obtained from mice immunized with PBS buffer alone (mean=0.6%; FIG. 7C). These results confirm that Ad-EVVLP can induce $CD4^+/CD8^+$ T cell responses against VLP and 3C protein.

2.6 Ad-EVVLP Vaccine Confers Protection Against CVA16 Infection in hSCARB2-Tg Mice In addition to the protection against EV71 infection, we investigated whether Ad-EVVLP or FI-EV71 can facilitate hSCARB2-Tg mice in resisting lethal CVA16 challenge. After Ad-EVVLP immunization, 100% of hSCARB2-Tg mice survived, in contrast to 0% survival of hSCARB2-Tg mice that received PBS or Ad-LacZ after CVA16 challenge (FIG. 8A and Table 3). Ad-EVVLP fully protected animals challenged with a 6-fold higher CVA16 dose ($3×10^6$ pfu) (Table 3). Consistent with our previous report [16,35], immunization with 1 µg FI-EV71 vaccine did not protect hSCARB2-Tg mice against $5×10^5$ pfu CVA16 challenge, leading to 0% survival (FIG. 8B and Table 3). Taken together, these results suggest that the Ad-EVVLP vaccine elicits potent $CD4^+/CD8^+$ T cell immune responses to control EV71 and CVA16, whereas the FI-EV71 vaccine protects against only EV71 challenge. This demonstrated a correlation with the results shown in Table 1, and the results of phase I clinical trials in which sera from subjects immunized with FI-EV71 vaccine neutralized distinct EV71 genotypes, but could not cross-neutralize CV [32,36].

TABLE 3

Ad-EVVLP protects hSCARB2-Tg mice from CVA16 challenge.

| | CVA16 (pfu) | Survival (%) |
|---|---|---|
| PBS | $5 × 10^5$ | 0 (6/6)* |
| Ad-LacZ | $5 × 10^5$ | 0 (6/6) |
| Ad-EVVLP | $5 × 10^5$ | 100 (10/10) |
| | $3 × 10^6$ | 100 (6/6) |
| FI-EV71 | $5 × 10^5$ | 0 (0/5) |

*hSCARB2-Tg mice were pre-immunized twice s.c. with PBS, $3 × 10^7$ pfu Ad-LacZ, $3 × 10^7$ pfu Ad-EVVLP, or 1 µg FI-EV71 vaccine on Days 1 and 7 after birth prior to being challenged s.c. with $5 × 10^5$ or $3 × 10^6$ pfu CVA16.
*Number of surviving mice per total number of tested mice is shown, and the survival rate was calculated.

3. Discussion:

In previous studies, EV71 subunit vaccines including DNA vaccine and recombinant VP1 protein induced an incomplete immune response and showed lower efficacy [19,37]. Oral vaccines, such as those against attenuated *Salmonella enterica* expressing EV71 VP1, have demonstrated limited efficacy against EV71, elevating the survival rates to only 50% after viral challenge [38]. Transgenic tomatoes [39] and peptide vaccines [40] expressing VP1 have also been developed, but the vaccine efficacy has not been assessed in vivo. A denatured virus particle containing formalin as a vaccine (FI-EV71) was tested in a hSCARB2-Tg mice model [16] and in human clinical trials [32], in which its safety and protective efficacy was demonstrated. A previous study on the development of influenza VLP as a vaccine showed that disrupting the influenza VLP structure abolished humoral immune responses and protective immunity [41]. In addition, the denatured EV71 particle possesses linear epitopes to elicit anti-EV71 antibodies; however, most of them are likely to be nonneutralizing, similar to the case of poliovirus [42]. Loss of the induction of effective neutralizing antibodies may be associated with the loss of antigenic determinants during inactivation, such as denatured EV71 particles by formalin. VLPs expressed in insect cells elicited even lower levels of neutralizing antibody titer, proliferation, and cytokine production in monkeys [35]. This may be due to differential post-translational modification of VLP proteins in nonhuman cells to induce differential immune responses. In contrast, intact VLPs produced from host cells preserve conformation-dependent epitopes, which might enable direct interaction of VLPs with B-cell receptors, activating B cells and antigen internalization through antigen-presenting cells [43]. This triggers potent antibody responses [44] and cross switching through cooperation with stimulated CD4$^+$ T cells [45]. Furthermore, recent studies have shown that neutralizing antibodies, specifically those against the EV71 capsid proteins, cannot cross-protect against CV infection [36,46], indicating that the vaccines currently being developed protect against only EV71-induced HFMD.

Figure 3:
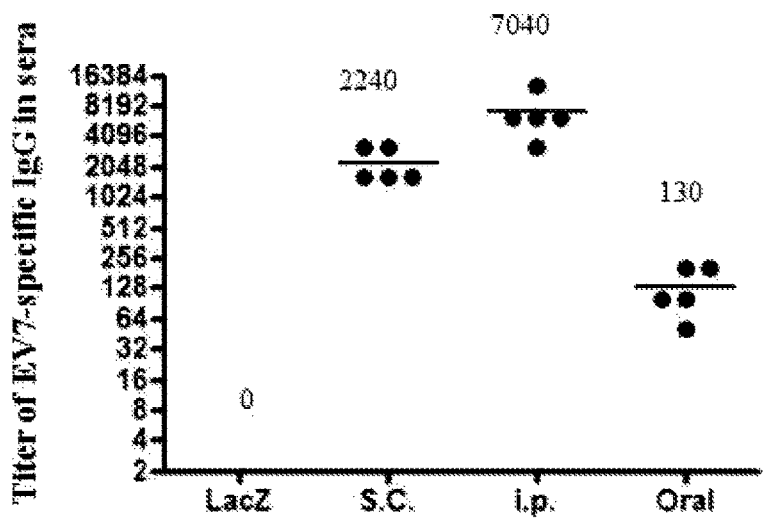
Figure 3:
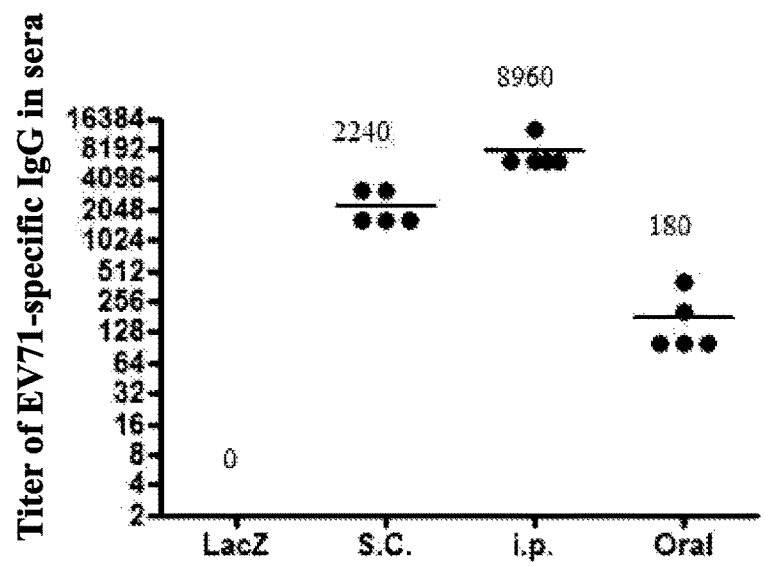

In this study, we evaluated the potential of adenovirus-expressing EV71 VLP as a vaccine candidate against EV71 and CVA16 infections through comparison with the efficacies and immune responses elicited by Ad-EVVLP and the classical preparation of formalin-inactivated EV71 vaccine Immunization with Ad-LacZ elicited no EV71-specific antibody titers and low levels of T cell responses, compared to Ad-EVVLP and FI-EV71 vaccines, which strongly induced the anti-EV71 antibody titer (FIG. 3, Table 1). Antibodies induced by Ad-EVVLP exhibited cross reactivity against the clinically isolated EV71 C2 and B4 genotypes (FIG. 3). In addition to anti-VLP antibody, the Ad-EVVLP vaccination induced anti-3C antibody (FIG. 7). However, we did not observe the neutralizing activity against CVA16 in the serum of Ad-EVVLP- and FI-EV71-immunized mice (Table 1). This may explain why the anti-3C antibody could not bind to the 3C protein, which was either not expressed or was in the EV71 or CV inner capsid.

Figure 12:
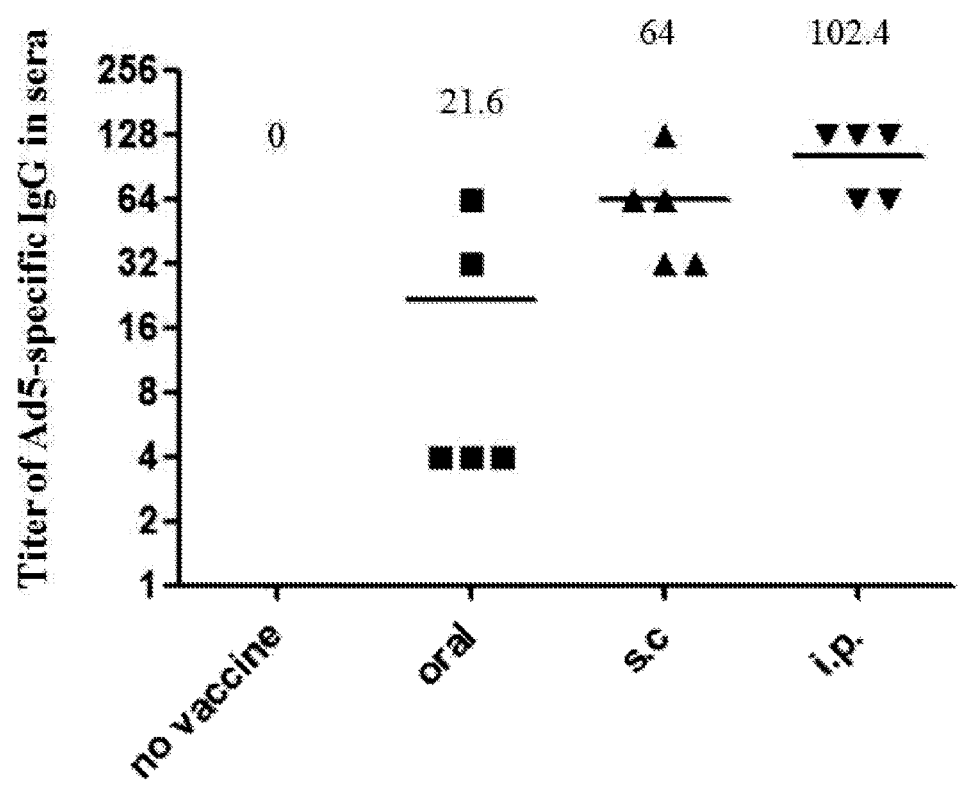
FIG. 12 shows induction of Ad5-specific IgG in the serum of Ad-vaccinated mice. Seven-week-old BALB/c mice were individually primed and boosted at 14-day intervals though oral, s.c., or i.p. routes with or without $10^8$ pfu Ad-EVVLP. Serum samples collected on Day 21 were assayed for IgG against heat-inactivated Ad5-immobilized ELISA. The results are expressed as titers for each test sample. Bars correspond to mean titers for each experimental group of 5 mice.

Previous studies have shown that preexisting anti-adenovirus antibodies do not affect subsequent generations of humoral responses to an antigen expressed through a mucosally administered recombinant adenovirus vector [47-49]. However, Ad-EVVLP oral immunization induced a decreased immune response compared to the mice receiving systemic Ad-EVVLP immunization (s.c. or i.p.; FIG. 3 and Table 1). Our results showed that the existence of low anti-Ad antibody in sera of vaccine-primed animals (FIG. 12) did not influence the secondary VLP-specific antibody in the sera of mice administered a second dose of Ad-EVVLP orally, s.c., or i.p. The actual immuno-efficacy of Ad-EVVLP still needs to be assessed in clinical trials.

Figure 4:
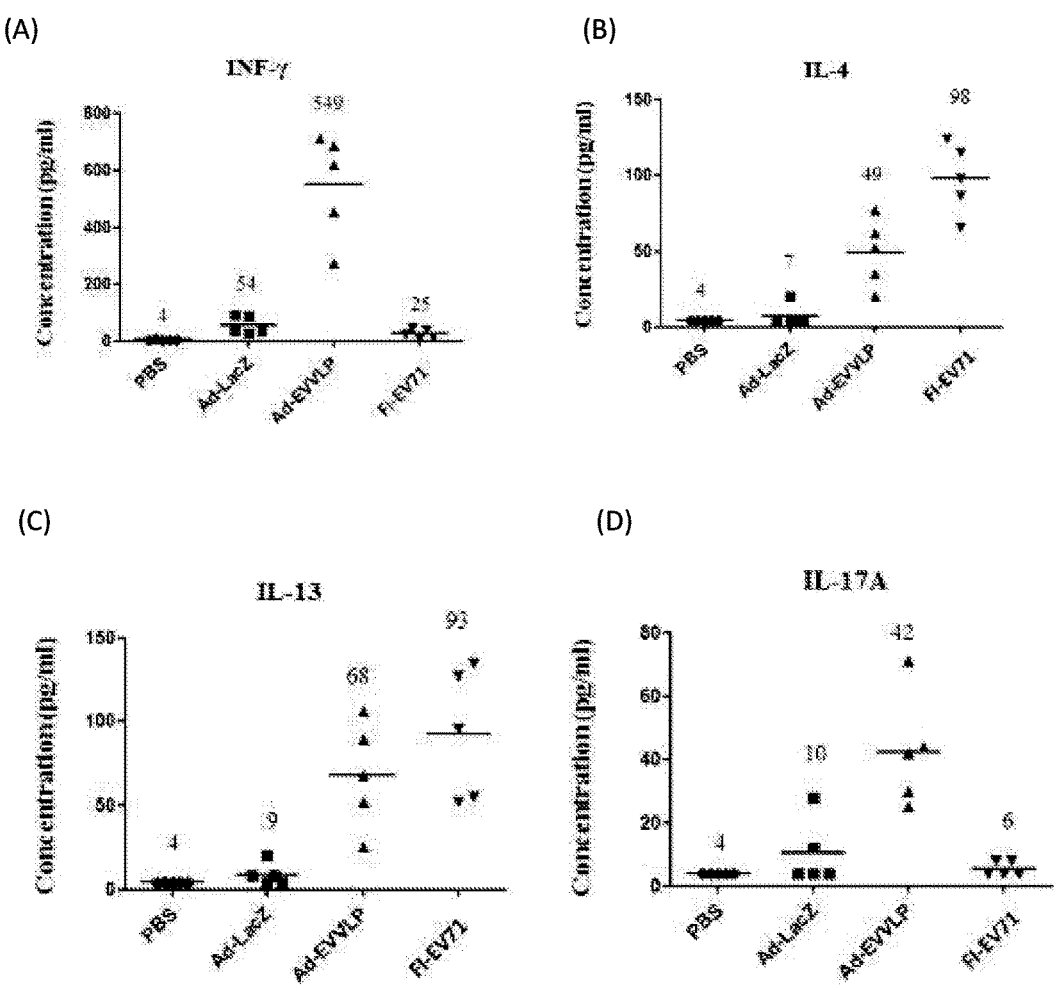

In addition to humoral responses, VLPs from other viruses have been reported to induce dendritic cell (DC) maturation and cytokine secretion [16,17], and can stimulate CD4$^+$ [18] and CD8$^+$ T cells [19,20]. Ad is a strong DC activator, which enzymatically processes and presents antigenic peptides associated with MHC class I and II molecules on the surface, and subsequently coordinates and stimulates T helper and cytotoxic T-cell responses [50]. Ad-EVVLP immunization induced capsid protein-specific cellular immune responses, which was confirmed by the EV71 VLP induction of CD4$^+$ and CD8$^+$ T cell activation (FIG. 5) and cytokine production (FIG. 4). Compared to FI-EV71 vaccine immunization that activated Th2-mediated responses [16] associated with IL-4 and IL-13 secretion (FIG. 4), the high IFN-γ, IL-4 and IL-13 levels produced by Ad-EVVLP-immunized splenocytes (FIG. 4) suggested a mixed Th1/Th2 immune response, which potentiates both the activation of effector cellular responses and antibody production. These results are consistent with the induction of Th1/Th2 immune responses from the VLP of the influenza virus [21] and human papillomavirus [51]. Conversely, the CD4$^+$ and CD8+ T cell activation corresponding to VLP was not observed in the FI-EV71-immunized mice (FIG. 5), indicating that the epitopic antigenicity of VLP in the FI-EV71 vaccine after formalin inactivation was changed from its native form of EV71 VLP. However, structural analysis has shown that FI-EV71 is not different from infectious EV71 virions [13], and immunogenicity studies have revealed that the formalin-inactivated F- and E-particles of EV71 can induce the neutralizing antibody, even though the F-particle was more potent than E-particles in mice [31]. Thus, the antigenicity of the Ad-EVVLP-expressed VLP compared to the FI-EV71 vaccine VLP in the activation of cellular responses will be investigated in the future.

Figure 8:
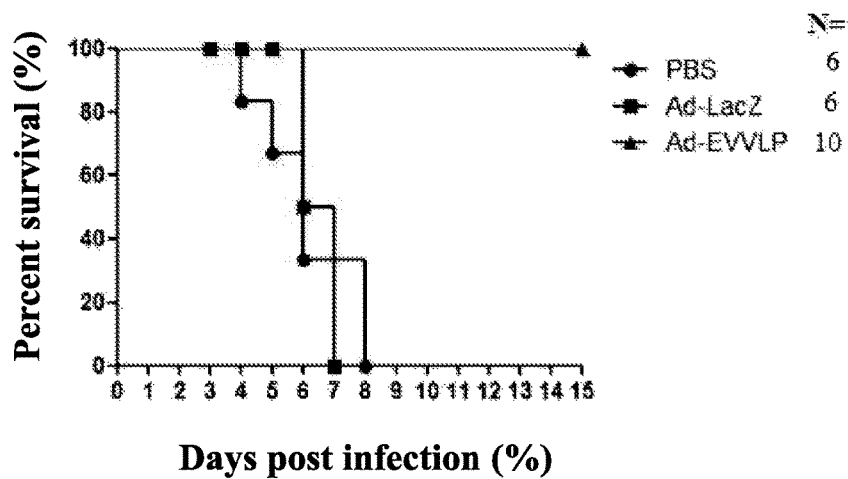
FIG. 8 shows that Ad-EVVLP but not FI-EV71 protects hSCARB2-Tg mice from CVA16 challenge. One-day-old hSCARB2-Tg mice were pre-immunized twice s.c. with (A) PBS (●), $3\times10^7$ pfu Ad-LacZ (■), or $3\times10^7$ (▲) pfu Ad-EVVLP, or (B) 1 µg FI-EV71 vaccine (●) on Days 1 and 7 after birth prior to being challenged s.c. with $5\times10^5$ pfu CVA16. The survival of mice was monitored on a daily basis for 15 days. The number (N) of transgenic mice is shown. A log-rank test was used for statistical analysis.
Figure 8:
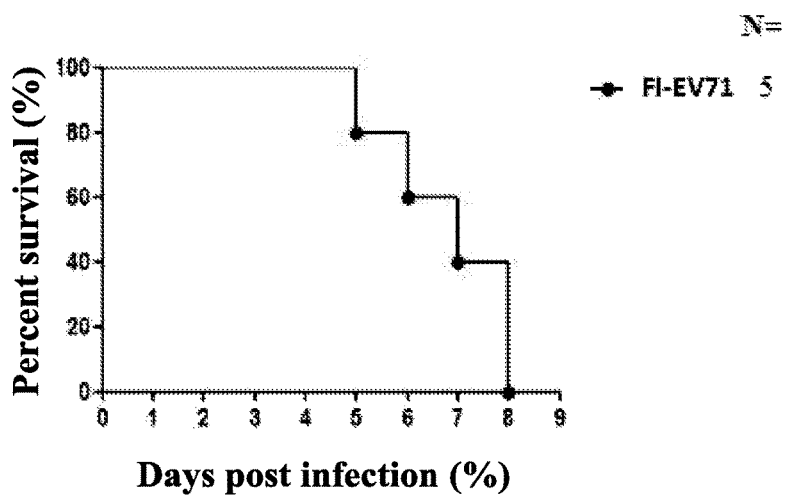
Figure 9:
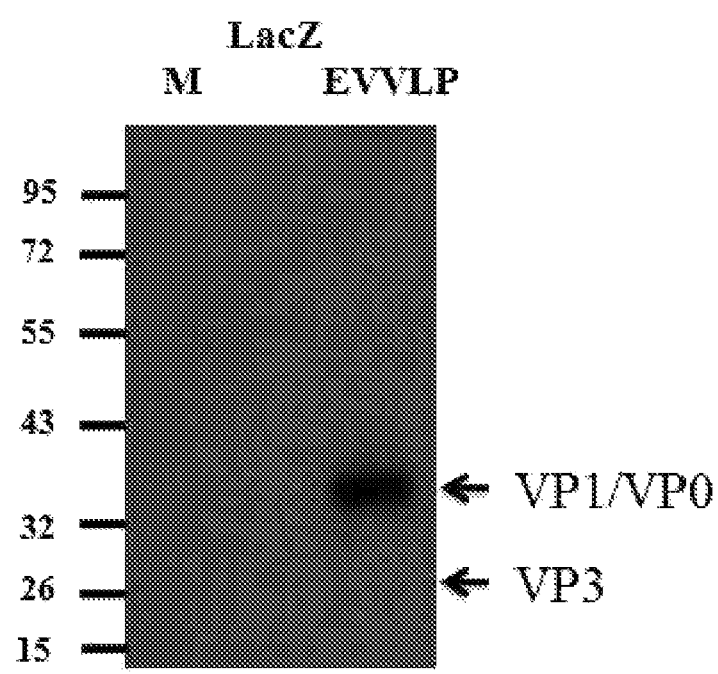
FIG. 9 shows immunoblotting of VLP expression in Ad-EVVLP-infected cells with serum from EV71-infected mice. The lysates of Ad-LacZ- and Ad-EVVLP-infected 293A cells were analyzed by immunoblotting with polyclonal serum from BALB/c mice i.p. injected with $10^6$ pfu EV71 5746. The protein marker (M) is marked.
Figure 13:
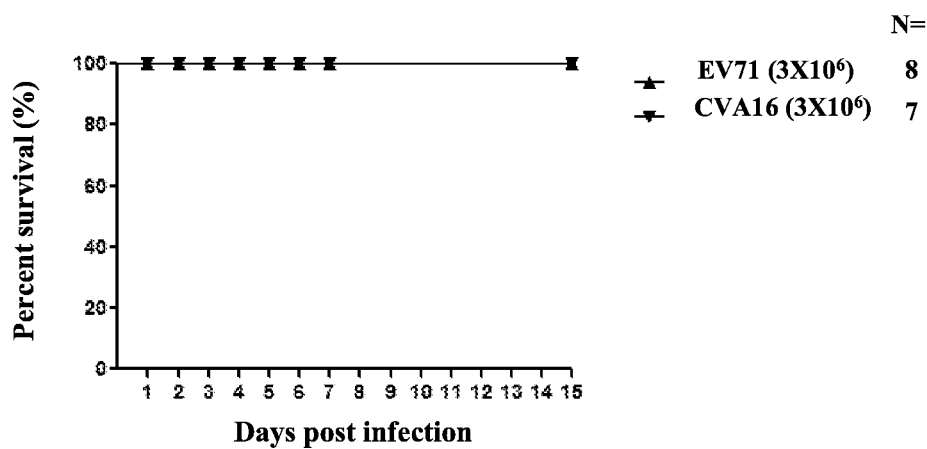
FIG. 13 shows that Ad-3CD protects hSCARB2-Tg mice from EV71 and CVA16 challenges. One-day-old hSCARB2-Tg mice were pre-immunized twice s.c. with $3\times10^7$ pfu Ad-3CD on Days 1 and 7 after birth prior to being challenged s.c. with $3\times10^6$ pfu (▲) EV71 or (▼) CVA16. Control group immunized with $3\times10^7$ pfu Ad-LacZ was performed and shown in Table 2. The survival of mice was monitored on a daily basis for 15 days. The number (N) of transgenic mice is shown.

CD4$^+$ and CD8$^+$ T cell-mediated cellular responses corresponding to the recombinant 3C protein in Ad-EVVLP- but not FI-EV71 vaccine-immunized mice was also observed (FIG. 7). We demonstrated that Ad-EVVLP immunization fully protected hSCARB2-Tg mice against EV71 (FIG. 6) and CVA16 challenge (FIG. 8 and Table 3). These results suggest that protection against EV71 infection through Ad-EVVLP is mediated by the induction of EV71-VLP-specific neutralizing antibodies, as well as VLP- and 3C-specific cellular immunities. The lower titer of neutralizing antibodies accompanied by higher transmission rates in children and infants indicates that neutralizing antibodies are crucial for the prevention of EV71 infection [52,53]. Our study also demonstrated that challenge of hSCARB2-Tg mice with EV71 followed by VP1 specific monoclonal antibody treatment might prevent EV71-induced pathology [46]. However, serum in 80% of EV71-infected patients contain neutralizing antibodies 1 day after illness onset; the level of antibody titer does not correlate with disease severity [54]. In contrast, cellular immune responses correlate with disease progression and clinical outcome [33,55]. Decreased cellular immunity is associated with increased disease severity in EV71 patients, whereas neutralizing antibodies display no difference between mild and severe cases [34]. These studies suggest that cellular immunity might be crucial in the protection against enterovirus infection. Our results showed that the 3C-specific cellular immunity induced by Ad-EVVLP might be sufficient to protect against CVA16 infection (FIG. 8 and Table 3) even though Ad-EVVLP did not induce a CVA16-VLP-specific neutralizing antibody (Table 1). Therefore, we constructed Ad-3CD only expressing the 3CD gene and immunized hSCARB2-Tg mice followed by EV71 or CVA16 challenge. The results showed that Ad-3CD fully protected animals from EV71 and CVA16 challenges (FIG. 13). They indicate that 3CD-specific cellular immunities are sufficient to provide protection against EV71 and CVA16 infections.

In conclusion, VLP expression in host cells through the replication of defective adenovirus mimicking the natural structure of EV71 particles induced antibodies against VLP and 3C proteins and cellular immunities specific to VLP and 3C proteins. Because the 3C protein is highly conserved between EV71 and CVA (Table 2), we demonstrated that Ad-EVVLP acts as a multivalent vaccine to suppress EV71 and CVA16-induced disease. We achieved several breakthroughs in the development of a medically necessary enterovirus vaccine. First, instead of the subunit EV71 vaccine, inactivated EV71 vaccine, or protein-typed VLPs that protect against only EV71-induced HFMD, Ad-EVVLP prevents EV71- and CVA-induced HFMD. Second, induction of 3C-specific cellular immunity might sufficiently protect against CVA infection.

Sequence Information

```
P1 of EV71
P1 (862 A.A)
                                                    (SEQ ID NO: 1)
MGSQVSTQRSGSHENSNSATEGSTINYTTINYYKDSVAATAGKQSLKQDPDKFANPVKDI

FTEMAAPLKSPSAEACGYSDRVAQLTIGNSTITTQEAANIIVGYGEWPSYCSDSDATAVD

KPTRPDVSVNRFYTLDTKLWEKSSKGWYWKFPDVLTETGVFGQNAQFHYLYRSGFCIHVQ

CNASKFHQGALLVAVLPEYVIGTVAGGTGTEDSHPPYKQTQPGADGFELQHPYVLDAGIP

ISQLTVCPHQWINLRINNCATIIVPYINALPFDSALNHCNFGLLVVPISPLDYDQGATPV

IPITITLAPMCFEFAGFRQAVTQGFPTELKPGTNQFLTTDDGVSAPILPNFHPTPCIHIP

GEVRNLLELCQVETILEVNNVPTNATSLMERLRFPVSAQAGKGELCAVFRADPGRSGPWQ

STLLGQLCGYYTQWSGSLEVTFMFTGSFMATGKMLIAYTPPGGPLPKDRATAMLGTDVIW

DFGLQSSVTLVIPWISNTHYRAHARDGVFDYYTTGLVSIWYQTNYVVPIGAPNTAYIIAL

AAAQKNFTMKLCKDASDILQTGTIQGDRVADVIESSIGDSVSRALTRALPAPTGQDTQVS

SHRLDTGKGPALQAAEIGASSNASDESMIETRCVLNSHSTAETTLDSFFSRAGLVGEIDL

PLEGTTNPNGYANWDIDITGYAQMRRKVELFTYMPFNAEITFVACTPTGEVVPQLLQYMF

VPPGAPKPDSRESLAWQTATNPSVFVKLSDPPAQVSVPFMSPASAYQWFYDGYPTFGEHK

QEKDLEYGACPNNMMGTFSVRTVGTSKSKCPLVIRIYMRMKHVRAWIPRPMRNQNYLFKA

NPNYAGNSIKPTGASRTAITTL

3CD of EV71
                                                    (SEQ ID NO: 2)
GPSLDFALSLLRRNIRQVQTDQGHFTMLGVRDHLAVLPRHSQPG

KTIWVEHKLVKIVDAVELVDEQGVNLELTLITLDTNEKFRDITRFIPETINPASDATL

VINTEHMPSMFVPVGDVVQYGFLNLSGKPTHRTMMYNFPTKAGQCGGVVTAVGKVIGI

HIGGNGRQGFCAALKRGYFCSEQGEIQWMKSNKETGRLNINGPTRTKLEPSVFHDVFE

GTKEPAVLTSKDPRLEVDFEQALFSKYVGNTLHEPDEFVKEAALHYANQLKQLDIKTT

KMSMEDACYGTENLEAIDLHTSAGYPYSALGIKKKDILDPTTRDVSRMKFYMDKYGLD

LPYSTYVKDELRAIDKIKKGKSRLIEASSLNDSVYLRMTFGHLYEAFHANPGTVTGSA

VGCNPDVFWSKLPILLPGSLFAFDYSGYDASLSPVWFRALEIVLREIGYSEDAVSLIE

GINHTHHVYRNKTYCVLGGMPSGCSGTSIFNSMINNIIRTLLIKTFKGIDLDELNMV

AYGDDVLASYPFPIDCLELARTGKEYGLTMTPADKSPCFNEVTWENATFLKRGFLPDH

QFPFLIHPTMPMREIHESIRWTKDARNTQDHVRSLCLLAWHNGKEEYEKFVSTIRSVP

IGKALAIPNFENLRRNWLELF 3C of EV71
                                                    (SEQ ID NO: 5)
GPSLDFALSLLRRNIRQVQTDQGHFTMLGVRDRLAVLPRHSQPGKTIWVEHKL

VKIVDAVELVDEQGVNLELTLVTLDTNEKFRDITRFIPETISPASDATLVINTEH

MPSMFVPVGDVVQYGFLNLSGKPTHRTMMYNFPTKAGQCGGVVTAVGKVIG

IHIGGNGRQGFCAALKRGYFCSEQ 3D of EV71
                                                    (SEQ ID NO: 6)
GEIQWMKPNKETGRLNINGPTRTKLEPSVFHDVELGTKEPAVLTSKDPRLEVD

FEQALFSKYVGNTLHEPDEFVKEAALHYANQLKQLDIKTTKMSMEDACYGT

ENLEAIDLHTSAGYPYSALGIKKKDILDPTTRDVSKMKFYMDKYGLDLPYST
```

-continued

```
YVKDELRAIDKIKKGKSRLIEASSLNDSVYLRMTFGHLYEAFHANPGTITGSA

VGCNPDVFWSKLPILLSGSLFAFDYSGYDASLSPVWFRALEIVLREIGYSEDAV

SLIEGINHTHHVYRNKTYCVLGGMPSGCSGTSIFNSMINNIIRTLLIKTFKGIDL

NELNMVAYGDDVLASYPFPIDCLELARTGKEYGLTMTPADKSPCFNEVTW

ENATFLKRGFLPDYQFPFLIHPTMPMREIHESIRWTKDARSTQDHVRSLCLLA

WLNGKEE YEKFVSAIRSVPIGKALAIPNYENLRRNWLELF
```

REFERENCES

1. Ho M, Chen E R, Hsu K H, Twu S J, Chen K T, Tsai S F, et al. An epidemic of enterovirus 71 infection in Taiwan. Taiwan Enterovirus Epidemic Working Group. N Engl J Med. 1999; 341: 929-935.
2. Wang S M, Liu C C, Tseng H W, Wang J R, Huang C C, Chen Y J, et al. Clinical spectrum of enterovirus 71 infection in children in southern Taiwan, with an emphasis on neurological complications. Clin Infect Dis. 1999; 29: 184-190.
3. Liu C C, Tseng H W, Wang S M, Wang J R, Su I J. An outbreak of enterovirus 71 infection in Taiwan, 1998: epidemiologic and clinical manifestations. J Clin Virol. 2000; 17: 23-30.
4. Perez-Velez C M, Anderson M S, Robinson C C, McFarland E J, Nix W A, Pallansch M A, et al. Outbreak of neurologic enterovirus type 71 disease: a diagnostic challenge. Clin Infect Dis. 2007; 45: 950-957.
5. Huang C C, Liu C C, Chang Y C, Chen C Y, Wang S T, Yeh T F. Neurologic complications in children with enterovirus 71 infection. N Engl J Med. 1999; 341: 936-942.
6. AbuBakar S, Chee H Y, Al-Kobaisi M F, Xiaoshan J, Chua K B, Lam S K. Identification of enterovirus 71 isolates from an outbreak of hand, foot and mouth disease (HFMD) with fatal cases of encephalomyelitis in Malaysia. Virus Res. 1999; 61: 1-9.
7. Lin K H, Hwang K P, Ke G M, Wang C F, Ke L Y, Hsu Y T, et al. Evolution of EV71 genogroup in Taiwan from 1998 to 2005: an emerging of subgenogroup C4 of EV71. J Med Virol. 2006; 78: 254-262.
8. Lu C H, Huang S W, Lai Y L, Lin C P, Shih C H, Huang C C, et al. On the relationship between the protein structure and protein dynamics. Proteins. 2008; 72: 625-634.
9. Melnick J L, Schmidt N J, Mirkovic R R, Chumakov M P, Lavrova I K, Voroshilova M K. Identification of Bulgarian strain 258 of enterovirus 71. Intervirology. 1980; 12: 297-302.
10. Nagy G, Takatsy S, Kukan E, Mihaly I, Domok I. Virological diagnosis of enterovirus type 71 infections: experiences gained during an epidemic of acute CNS diseases in Hungary in 1978. Arch Virol. 1982; 71: 217-227.
11. Wu T N, Tsai S F, Li S F, Lee T F, Huang T M, Wang M L, et al. Sentinel surveillance for enterovirus 71, Taiwan, 1998. Emerg Infect Dis. 1999; 5: 458-460.
12. McMinn P C. An overview of the evolution of enterovirus 71 and its clinical and public health significance. FEMS Microbiol Rev. 2002; 26: 91-107.
13. Wang X, Peng W, Ren J, Hu Z, Xu J, Lou Z, et al. A sensor-adaptor mechanism for enterovirus uncoating from structures of EV71. Nat Struct Mol Biol. 2012; 19: 424-429.
14. Yamayoshi S, Yamashita Y, Li J, Hanagata N, Minowa T, Takemura T, et al. Scavenger receptor B2 is a cellular receptor for enterovirus 71. Nat Med. 2009; 15: 798-801.
15. Nishimura Y, Shimojima M, Tano Y, Miyamura T, Wakita T, Shimizu H. Human P-selectin glycoprotein ligand-1 is a functional receptor for enterovirus 71. Nat Med. 2009; 15: 794-797.
16. Lin Y W, Yu S L, Shao H Y, Lin H Y, Liu C C, Hsiao K N, et al. Human SCARB2 transgenic mice as an infectious animal model for enterovirus 71. PLoS One. 2013; 8: e57591.
17. Fujii K, Nagata N, Sato Y, Ong K C, Wong K T, Yamayoshi S, et al. Transgenic mouse model for the study of enterovirus 71 neuropathogenesis. Proc Natl Acad Sci USA. 2013; 110: 14753-14758.
18. Chang J Y, Chang C P, Tsai H H, Lee C D, Lian W C, Ih Jen S, et al. Selection and characterization of vaccine strain for Enterovirus 71 vaccine development. Vaccine. 30: 703-711.
19. Wu C N, Lin Y C, Fann C, Liao N S, Shih S R, Ho M S. Protection against lethal enterovirus 71 infection in newborn mice by passive immunization with subunit VP1 vaccines and inactivated virus. Vaccine. 2001; 20: 895-904.
20. Chung Y C, Ho M S, Wu J C, Chen W J, Huang J H, Chou S T, et al Immunization with virus-like particles of enterovirus 71 elicits potent immune responses and protects mice against lethal challenge. Vaccine. 2008; 26: 1855-1862.
21. Wang Y F, Chou C T, Lei H Y, Liu C C, Wang S M, Yan J J, et al. A mouse-adapted enterovirus 71 strain causes neurological disease in mice after oral infection. J Virol. 2004; 78: 7916-7924.
22. Khong W X, Yan B, Yeo H, Tan E L, Lee J J, Ng J K, et al. A non mouse-adapted Enterovirus 71 (EV71) strain exhibits neurotropism causing neurological manifestations in a novel mouse model of EV71 infection. J Virol. 2012.
23. Wu S C, Liu C C, Lian W C. Optimization of microcarrier cell culture process for the inactivated enterovirus type 71 vaccine development. Vaccine. 2004; 22: 3858-3864.
24. Liu C C, Lian W C, Butler M, Wu S C. High immunogenic enterovirus 71 strain and its production using serum-free microcarrier Vero cell culture. Vaccine. 2007; 25: 19-24.
25. Lin Y W, Lin H Y, Tsou Y L, Chitra E, Hsiao K N, Shao H Y, et al. Human SCARB2-mediated entry and endocytosis of EV71. PLoS One. 2012; 7: e30507.
26. Liu C C, Chou A H, Lien S P, Lin H Y, Liu S J, Chang J Y, et al. Identification and characterization of a cross-neutralization epitope of Enterovirus 71. Vaccine. 2011; 29: 4362-4372.

27. Mizuguchi H, Kay M A. Efficient construction of a recombinant adenovirus vector by an improved in vitro ligation method. Hum Gene Ther. 1998; 9: 2577-2583.
28. Bradford M M. A rapid and sensitive method for the quantitation of microgram quantities of protein utilizing the principle of protein-dye binding. Analytical biochemistry. 1976; 72: 248-254.
29. Reed L J M H. A simple method of estimating 50 percent end-points. Am J Hyg. 1938; 27: 493-497.
30. Fundamental Virology. Fourth Edition ed.: Lippincott Williams and Wilkins; 2001.
31. Liu C C, Guo M S, Lin F H, Hsiao K N, Chang K H, Chou A H, et al. Purification and characterization of enterovirus 71 viral particles produced from vero cells grown in a serum-free microcarrier bioreactor system. PLoS One. 2011; 6: e20005.
32. Liu C C, Chow Y H, Chong P, Klein M. Prospect and challenges for the development of multivalent vaccines against hand, foot and mouth diseases. Vaccine. 2014 DOI: 10.1016/j.vaccine.2014.08.064.
33. Yang K D, Yang M Y, Li C C, Lin S F, Chong M C, Wang C L, et al. Altered cellular but not humoral reactions in children with complicated enterovirus 71 infections in Taiwan. J Infect Dis. 2001; 183: 850-856.
34. Chang L Y, Hsiung C A, Lu C Y, Lin T Y, Huang F Y, Lai Y H, et al. Status of cellular rather than humoral immunity is correlated with clinical outcome of enterovirus 71. Pediatric research. 2006; 60: 466-471.
35. Lin Y L, Yu C I, Hu Y C, Tsai T J, Kuo Y C, Chi W K, et al. Enterovirus type 71 neutralizing antibodies in the serum of macaque monkeys immunized with EV71 virus-like particles. Vaccine. 2012; 30: 1305-1312.
36. Chou A H, Liu C C, Chang J Y, Jiang R, Hsieh Y C, Tsao A, et al. Formalin-Inactivated EV71 Vaccine Candidate Induced Cross-Neutralizing Antibody against Subgenotypes B1, B4, B5 and C4A in Adult Volunteers. PLoS One. 2013; 8: e79783.
37. Lee M S, Chang L Y. Development of enterovirus 71 vaccines. Expert Rev Vaccines. 2010; 9: 149-156.
38. Chiu C H, Chu C, He C C, Lin T Y. Protection of neonatal mice from lethal enterovirus 71 infection by maternal immunization with attenuated *Salmonella enterica* serovar *Typhimurium* expressing VP1 of enterovirus 71. Microbes and infection/Institut Pasteur. 2006; 8: 1671-1678.
39. Chen H F, Chang M H, Chiang B L, Jeng S T. Oral immunization of mice using transgenic tomato fruit expressing VP1 protein from enterovirus 71. Vaccine. 2006; 24: 2944-2951.
40. Foo D G, Alonso S, Phoon M C, Ramachandran N P, Chow V T, Poh C L. Identification of neutralizing linear epitopes from the VP1 capsid protein of Enterovirus 71 using synthetic peptides. Virus Res. 2007; 125: 61-68.
41. Quan F S, Huang C, Compans R W, Kang S M. Virus-like particle vaccine induces protective immunity against homologous and heterologous strains of influenza virus. J Virol. 2007; 81: 3514-3524.
42. Muir P, Kammerer U, Korn K, Mulders M N, Poyry T, Weissbrich B, et al. Molecular typing of enteroviruses: current status and future requirements. The European Union Concerted Action on Virus Meningitis and Encephalitis. Clinical microbiology reviews. 1998; 11: 202-227.
43. Denis J, Majeau N, Acosta-Ramirez E, Savard C, Bedard M C, Simard S, et al. Immunogenicity of *papaya* mosaic virus-like particles fused to a hepatitis C virus epitope: evidence for the critical function of multimerization. Virology. 2007; 363: 59-68.
44. Zinkernagel R M. On natural and artificial vaccinations. Annual review of immunology. 2003; 21: 515-546.
45. Gamvrellis A, Leong D, Hanley J C, Xiang S D, Mottram P, Plebanski M. Vaccines that facilitate antigen entry into dendritic cells. Immunology and cell biology. 2004; 82: 506-516.
46. Chang H W, Lin Y W, Ho H M, Lin M H, Liu C C, Shao H Y, et al. Protective efficacy of VP1-specific neutralizing antibody associated with a reduction of viral load and pro-inflammatory cytokines in human SCARB2-transgenic mice. PLoS One. 2013; 8: e69858.
47. Xiang Z Q, Gao G P, Reyes-Sandoval A, Li Y, Wilson J M, Ertl H C. Oral vaccination of mice with adenoviral vectors is not impaired by preexisting immunity to the vaccine carrier. J Virol. 2003; 77: 10780-10789.
48. McCoy K, Tatsis N, Korioth-Schmitz B, Lasaro M O, Hensley S E, Lin S W, et al. Effect of preexisting immunity to adenovirus human serotype 5 antigens on the immune responses of nonhuman primates to vaccine regimens based on human- or chimpanzee-derived adenovirus vectors. J Virol. 2007; 81: 6594-6604.
49. Shao H Y, Yu S L, Sia C, Chen Y, Chitra E, Chen I H, et al Immunogenic properties of RSV-B1 fusion (F) protein gene-encoding recombinant adenoviruses. Vaccine. 2009 DOI: 50264-410X(09)00992-X[pii]10.1016/j.vaccine.2009.07.004.
50. Barouch D H, Nabel G J. Adenovirus vector-based vaccines for human immunodeficiency virus type 1. Human gene therapy. 2005; 16: 149-156.
51. Evans T G, Bonnez W, Rose R C, Koenig S, Demeter L, Suzich J A, et al. A Phase 1 study of a recombinant viruslike particle vaccine against human papillomavirus type 11 in healthy adult volunteers. J Infect Dis. 2001; 183: 1485-1493.
52. Chang L Y, King C C, Hsu K H, Ning H C, Tsao K C, Li C C, et al. Risk factors of enterovirus 71 infection and associated hand, foot, and mouth disease/herpangina in children during an epidemic in Taiwan. Pediatrics. 2002; 109: e88.
53. Chang L Y, Tsao K C, Hsia S H, Shih S R, Huang C G, Chan W K, et al. Transmission and clinical features of enterovirus 71 infections in household contacts in Taiwan. JAMA. 2004; 291: 222-227.
54. Yang C, Deng C, Wan J, Zhu L, Leng Q. Neutralizing antibody response in the patients with hand, foot and mouth disease to enterovirus 71 and its clinical implications. Virol J. 2011; 8: 306.
55. Chang L Y, Chang I S, Chen W J, Huang Y C, Chen G W, Shih S R, et al. HLA-A33 is associated with susceptibility to enterovirus 71 infection. Pediatrics. 2008; 122: 1271-1276.

What is claimed is:

1. A method of inducing an immune response in a subject against enterovirus infection, comprising administering to the subject an effective amount of a recombinant adenoviral vector, which comprises an expression cassette comprising the nucleic acid sequence of SEQ ID NO: 3 or 4.

2. The method of claim 1, wherein the recombinant adenoviral vector is replication deficient.

3. The method of claim 1, wherein the recombinant adenoviral vector is formulated in a vaccine composition.

4. The method of claim 1, wherein the enterovirus infection is caused by enterovirus 71 or coxsackievirus A group.

5. The method of claim 1, wherein the recombinant adenoviral vector is administered subcutaneously, nasally, intraperitoneally or orally.

6. The method of claim 1, wherein the administering is repeated.

7. The method of claim 1, wherein the immune response includes T cell responses against the enterovirus infection.

8. The method of claim 7, wherein the T cell response is 3C or 3CD specific.

* * * * *